US008749356B2

(12) United States Patent
Hussain et al.

(10) Patent No.: US 8,749,356 B2
(45) Date of Patent: Jun. 10, 2014

(54) RFID ENABLED DRAWER REFRIGERATION SYSTEM

(75) Inventors: Shariq Hussain, Vista, CA (US); Paul M. Elizondo, Escondido, CA (US); Timothy Golde, Forest Ranch, CA (US); Jimmy Caputo, Carlsbad, CA (US)

(73) Assignee: MEPS Real-Time, Inc., Carlsbad, CA (US)

( * ) Notice: Subject to any disclaimer, the term of this patent is extended or adjusted under 35 U.S.C. 154(b) by 77 days.

(21) Appl. No.: 13/310,569

(22) Filed: Dec. 2, 2011

(65) Prior Publication Data

US 2012/0137706 A1 Jun. 7, 2012

Related U.S. Application Data

(63) Continuation-in-part of application No. 12/631,861, filed on Dec. 7, 2009, now Pat. No. 8,384,545.

(60) Provisional application No. 61/419,762, filed on Dec. 3, 2010.

(51) Int. Cl.
*H04Q 5/22* (2006.01)
*G06F 19/00* (2011.01)

(52) U.S. Cl.
CPC .................................. *G06F 19/3462* (2013.01)
USPC ................... 340/10.42; 340/10.1; 340/572.1; 340/572.4; 340/572.7; 340/572.8; 700/231; 700/235

(58) Field of Classification Search
CPC .................................................. G06F 19/3462
USPC .......... 340/10.42, 10.1, 572.11, 572.4, 572.7, 340/572.8; 700/231, 235
See application file for complete search history.

(56) References Cited

U.S. PATENT DOCUMENTS

| 8,398,184 | B1* | 3/2013 | Benneche et al. ............. 312/292 |
| 2007/0008113 | A1 | 1/2007 | Spoonhower et al. |
| 2008/0094214 | A1 | 4/2008 | Azevedo et al. |
| 2008/0172253 | A1 | 7/2008 | Chung et al. |
| 2009/0159608 | A1 | 6/2009 | Shoenfeld |
| 2010/0300130 | A1 | 12/2010 | Shoenfeld et al. |
| 2011/0172815 | A1* | 7/2011 | Kim .............................. 700/235 |

OTHER PUBLICATIONS

International Search Report dated Jun. 28, 2012 from International Application No. PCT/US2011/063162 filed Dec. 2, 2011.

\* cited by examiner

*Primary Examiner* — Tai T Nguyen
(74) *Attorney, Agent, or Firm* — Thomas A. Runk; Fulwider Patton LLP

(57) ABSTRACT

An automated system and associated method for storing medical items comprises a medication cabinet having at least one refrigerated drawer having a thermo-electric cooling (TEC) device and a non-refrigerated drawer. The refrigerated drawer design is such that cooling gradients throughout the drawer are minimized. Faraday cages are provided about each drawer to support separate RFID readers to monitor the medical items in each drawer. An automatic RFID data detection system determines the temperature requirements of medical items in the refrigerated drawer and controls the TEC device to maintain the required temperature. A temperature logging system for the refrigerated drawer is provided. A separate RFID reader determines if a temperature-controlled item has been placed in a non-refrigerated drawer and if so, an alert is provided.

20 Claims, 21 Drawing Sheets

RFID ENABLED DRAWER REFRIGERATION SYSTEM

CROSS REFERENCES TO RELATED APPLICATIONS

This application is a continuation-in-part of U.S. application Ser. No. 12/631,861, filed Dec. 7, 2010, now U.S. Pat. No. 8,384,545, and claims the benefit of U.S. Application No. 61/419,762, filed on Dec. 3, 2010, all of which are incorporated herein by reference. Applicant also incorporates U.S. Application No. 61/302,912 herein by reference.

BACKGROUND

The invention relates generally to the field of medication administration, and more particularly, to a medication administration system and associated method that provide identification, tracking, and temperature control over medications.

Medication dispensing systems have been in use for many years. The initial purpose of such systems was to reduce medication errors associated with manual distribution and the high cost of maintaining a large amount of inventory. Current systems present many advantages, including lower costs associated with pharmaceutical distribution, improved inventory control, substance control, automated documentation, further reduction of errors, and relieving professional pharmacists and nursing personnel of many tasks.

In large medical facilities, the main inventories of pharmaceutical items are held in storage locations which are often far removed from the patients who use them. To facilitate secure and accurate delivery of the pharmaceutical items from these storage locations to the patient, a variety of systems have been proposed and put into use. In earlier systems, referred to as a "cart exchange" system, medication carts are distributed at nursing stations in the medical facility, remote from the central pharmacy, and are periodically exchanged with fully supplied carts. Typically these carts contain a twenty-four hour supply of medications sorted by patient into specific drawers. The "used" cart is returned to a central pharmacy of supply area where the next twenty-four hours of medications are replenished. Narcotics, are stored in locked boxes on the floor, requiring two nurses with separate keys and a written log.

While the cart exchange system is still in use for some medications, the activities of bringing up many new orders from the central pharmacy during the day, and having a large amount of unused medication being returned results in a large amount of labor. The re-stocking of these medications needs to be done accurately, and is very time consuming. As a result there has been an increasing use of automated, processor-based, medication cabinets on the nursing floors. The processor on each cabinet monitors the access to the pharmaceutical items in these fixed cabinets, allowing the current on-hand inventory and the need for replenishment to be communicated to a central processor at the central pharmacy location. These processor-based dispensing cabinets were initially used for the more convenient management of narcotics, and for the ability to have a "floor stock" of common medications from which a nurse could issue the first dose of a needed new prescription, while waiting for the twenty-four hours supply to be delivered from the pharmacy in the exchange cart, or on a special order basis.

Referring now to FIG. 23 the medication cabinet 300 typically comprises an integrated touch screen 304 coupled to a control unit 306, a communication link 308 for linking to a central server 310, and a communication link 314 for linking to one or more carts 316. Such communication links 308 and 314 are schematically shown as connections for wired communication, but could also be transmitters and receivers (e.g., RF, IR, acoustical) for wireless communication as would be recognized by one of ordinary skill in communication technologies. In addition to the data that is input via the communication links 308 and 314, data is input manually via a virtual keyboard included in the touch screen 304. The communication link 308 is a connection to the server 310 and allows the medication cabinet 300 to interface with the data base 320 to which the server 310 has access for real-time updates, as needed. It also provides necessary information to guide the pre-authorized healthcare attendant in the preparation of patient medications, intravenous solutions, and the like. In an alternative embodiment shown in FIG. 24, an actual keyboard 322 or keypad, or similar device, may replace or augment the functions of the touch screen 304.

These processor-based medication cabinets 300 offer the possibility of storing the majority of medications that the patients on the floor might need during the day and night. In many cases, these medications are stored in pockets within locked drawers. A nurse, upon entering his or her own personal ID, and the ID of a specific patient, will see the medications that are approved overall for that selected patient and will also see what medications are due at that particular time, referred to generally as "Due Medications." The task for the central pharmacy then is to monitor the on-hand stock of the medications stored in the cabinets, and restock those levels at regular intervals. A significant advantage of this process is not having unused doses of medications returned to the central pharmacy. It also means that first doses (as well as subsequent doses) are immediately available.

There are still many situations that continue to require medications to be brought from the central pharmacy. For example, to avoid medication errors, intravenous fluids (IVs) that contain medication may be mixed in the pharmacy and brought up to the floor for safety reasons, rather than being prepared by nurses by attaching a so-called piggy-back medication bag to a standard diluent bag. There are also specialized, or infrequently-used medications, or those with short life, or requiring refrigeration, or that need special handling from the pharmacy. Many medicines and vaccines are temperature sensitive and have precise storage requirements. Some medical compositions having low stability need to be maintained under low temperature, perhaps within the range of 2 to 6 degrees Celsius. Typically where cooling is required, a separate medication cabinet is used that includes a refrigeration unit.

Present medication cabinets are either entirely refrigerated or non-refrigerated. Every drawer in these cabinets experiences the same refrigeration, or lack thereof, depending on the cabinet. Refrigeration is relatively expensive due to the power requirements and the refrigeration devices needed. Medication cabinets as a whole are expensive and relatively large, each having its own computer equipment, power equipment, communication equipment, and each taking up valuable floor space. In many cases in the prior art where some patients require medications that must be refrigerated prior to administration, as well as medications that should not be refrigerated, two cabinets are required, one of which is refrigerated and the other of which is non-refrigerated. In some cases, only a small portion of a refrigerated cabinet is needed yet refrigeration is provided to the entire cabinet, a large portion of which is empty. This is an inefficient approach. While the current systems provide working methods for issuing refrigerated medications, it would be desirable to reduce the cost of the cabinet drawers, allowing more items to be kept in a single cabinet that has both refrigerated and non-refrigerated drawers. It would therefore be beneficial from both a cost standpoint and a space standpoint to have both refrigerated and non-refrigerated drawers in a single cabinet.

It is also desirable to be able to track the temperature of the refrigerator or other temperature-controlled cabinet or drawer and record the tracked temperature over time in a log. Such tracking and record keeping may be strongly recommended or required by some healthcare organizations, such as the Joint Commission on Accreditation of Healthcare Organizations (JCAHO). It is also desirable to be able to automatically provide an alert if the temperature (or relative humidity) is outside an acceptable range for the medications requiring temperature control.

The handling of temperature controlled medications has also been a manual process in determining which medication requires temperature control and under what conditions it must be stored. Such manual handling, examination, and research is time consuming. It would be desirable to provide a system and method that can automate at least some of these requirements so that efficiency is increased.

Hence, those skilled in the art have recognized a need for and automated system and method for recognizing which medications require refrigeration, determining what level of refrigeration is required, and effecting such refrigeration. Those of skill in the art have also recognized the need to track the temperature of the refrigerator or other temperature-controlled cabinet or drawer in which temperature-controlled medications are kept and record the tracked temperature over time in a log. Those of skill in the art have further recognized the need for having both refrigerated and non-refrigerated drawers in a single cabinet so that expense and requirements for space are both reduced. The present invention fulfills these needs and others.

Radio-frequency identification ("RFID") is the use of electromagnetic energy ("EM energy") to stimulate a responsive device (known as an RFID "tag" or transponder) to identify itself and in some cases, provide additionally stored data. RFID tags typically include a semiconductor device having a memory, circuitry, and one or more conductive traces that form an antenna. Typically, RFID tags act as transponders, providing information stored in the semiconductor device memory in response to an RF interrogation signal received from a reader, also referred to as an interrogator. Some RFID tags include security measures, such as passwords and/or encryption. Many RFID tags also permit information to be written or stored in the semiconductor memory via an RF signal.

RFID tags may be incorporated into or attached to articles to be tracked. In some cases, the tag may be attached to the outside of an article with adhesive, tape, or other means and in other cases, the tag may be inserted within the article, such as being included in the packaging, located within the container of the article, or sewn into a garment. The RFID tags are manufactured with a unique identification number which is typically a simple serial number of a few bytes with a check digit attached. This identification number is incorporated into the tag during manufacture. The user cannot alter this serial/identification number and manufacturers guarantee that each serial number is used only once. This configuration represents the low cost end of the technology in that the RFID tag is read-only and it responds to an interrogation signal only with its identification number. Typically, the tag continuously responds with its identification number. Data transmission to the tag is not possible. These tags are very low cost and are produced in enormous quantities.

Such read-only RFID tags typically are permanently attached to an article to be tracked and, once attached, the serial number of the tag is associated with its host article in a computer data base. For example, a particular type of medicine may be contained in hundreds or thousands of small vials. Upon manufacture, or receipt of the vials at a health care institution, an RFID tag is attached to each vial. Each vial with its permanently attached RFID tag will be checked into the data base of the health care institution upon receipt. The RFID identification number may be associated in the data base with the type of medicine, size of the dose in the vial, and perhaps other information such as the expiration date of the medicine. Thereafter, when the RFID tag of a vial is interrogated and its identification number read, the data base of the health care institution can match that identification number with its stored data about the vial. The contents of the vial can then be determined as well as any other characteristics that have been stored in the data base. This system requires that the institution maintain a comprehensive data base regarding the articles in inventory rather than incorporating such data into an RFID tag.

An object of the tag is to associate it with an article throughout the article's life in a particular facility, such as a manufacturing facility, a transport vehicle, a health care facility, a storage area, or other, so that the article may be located, identified, and tracked, as it is moved. For example, knowing where certain medical articles reside at all times in a health care facility can greatly facilitate locating needed medical supplies when emergencies arise. Similarly, tracking the articles through the facility can assist in generating more efficient dispensing and inventory control systems as well as improving work flow in a facility. Additionally, expiration dates can be monitored and those articles that are older and about to expire can be moved to the front of the line for immediate dispensing. This results in better inventory control and lowered costs.

Other RFID tags are writable and information about the article to which the RFID tag is attached can be programmed into the individual tag. While this can provide a distinct advantage when a facility's computer servers are unavailable, such tags cost more, depending on the size of the memory in the tag. Programming each one of the tags with information contained in the article to which they are attached involves further expense.

RFID tags may be applied to containers or articles to be tracked by the manufacturer, the receiving party, or others. In some cases where a manufacturer applies the tags to the product, the manufacturer will also supply a respective data base file that links the identification number of each of the tags to the contents of each respective article. That manufacturer supplied data base can be distributed to the customer in the form of a file that may easily be imported into the customer's overall data base thereby saving the customer from the expense of creating the data base.

Many RFID tags used today are passive in that they do not have a battery or other autonomous power supply and instead, must rely on the interrogating energy provided by an RFID reader to provide power to activate the tag. Passive RFID tags require an electromagnetic field of energy of a certain frequency range and certain minimum intensity in order to achieve activation of the tag and transmission of its stored data. Another choice is an active RFID tag; however, such tags require an accompanying battery to provide power to activate the tag, thus increasing the expense of the tag and making them undesirable for use in a large number of applications.

Depending on the requirements of the RFID tag application, such as the physical size of the articles to be identified, their location, and the ability to reach them easily, tags may need to be read from a short distance or a long distance by an RFID reader. Such distances may vary from a few centimeters to ten or more meters. Additionally, in the U.S. and in other countries, the frequency range within which such tags are permitted to operate is limited. As an example, lower frequency bands, such as 125 KHz and 13.56 MHz, may be used for RFID tags in some applications. At this frequency range, the electromagnetic energy is less affected by liquids and other dielectric materials, but suffers from the limitation of a short interrogating distance. At higher frequency bands where RFID use is permitted, such as 915 MHz and 2.4 GHz, the RFID tags can be interrogated at longer distances, but they de-tune more rapidly as the material to which the tag is attached varies. It has also been found that at these higher frequencies, closely spaced RFID tags will de-tune each other as the spacing between tags is decreased.

There are a number of common situations where the RFID tags may be located inside enclosures. Some of these enclosures may have entirely or partially metal or metallized surfaces. Examples of enclosures include metal enclosures (e.g., shipping containers), partial metal enclosures (e.g., vehicles such as airplanes, buses, trains, and ships that have a housing made from a combination of metal and other materials), and non-metal enclosures (e.g., warehouses and buildings made of wood). Examples of objects with RFID tags that may be located in these enclosures include loose articles, packaged articles, parcels inside warehouses, inventory items inside buildings, various goods inside retail stores, and various portable items (e.g., passenger identification cards and tickets, baggage, cargo, individual life-saving equipment such as life jackets and masks) inside vehicles, etc.

The read range (i.e., the range of the interrogation and/or response signals) of RFID tags is limited. For example, some types of passive RFID tags have a maximum range of about twelve meters, which may be attained only in ideal free space conditions with favorable antenna orientation. In a real situation, the observed tag range is often six meters or less. Therefore, some of the enclosures described above may have dimensions that far exceed the read range of an individual RFID tag. Unless the RFID reader can be placed in close proximity to a target RFID tag in such an enclosure, the tag will not be activated and read. Additionally, metal surfaces of the enclosures present a serious obstacle for the RF signals that need to be exchanged between RFID readers and RFID tags, making RFID tags located behind those metal surfaces difficult or impossible to detect.

In addition to the above, the detection range of the RFID systems is typically limited by signal strength to short ranges, frequently less than about thirty centimeters for 13.56 MHz systems. Therefore, portable reader units may need to be moved past a group of tagged items in order to detect all the tagged items, particularly where the tagged items are stored in a space significantly greater than the detection range of a stationary or fixed single reader antenna. Alternately, a large reader antenna with sufficient power and range to detect a larger number of tagged items may be used. However, such an antenna may be unwieldy and may increase the range of the radiated power beyond allowable limits. Furthermore, these reader antennae are often located in stores or other locations where space is at a premium and it is expensive and inconvenient to use such large reader antennae. In another possible solution, multiple small antennae may be used but such a configuration may be awkward to set up when space is at a premium and when wiring is preferred or required to be hidden.

In the case of medical supplies and devices, it is desirable to develop accurate tracking, inventory control systems, and dispensing systems so that RFID tagged devices and articles may be located quickly should the need arise, and may be identified for other purposes, such as expiration dates. In the case of medical supply or dispensing cabinets used in a health care facility, a large number of medical devices and articles are located closely together, such as in a plurality of drawers. Cabinets such as these are typically made of metal, which can make the use of an external RFID system for identification of the stored articles difficult. In some cases, such cabinets are locked due to the presence of narcotics or other medical articles or apparatus within them that are subject to a high theft rate. Thus, manual identification of the cabinet contents is difficult due to the need to control access.

Providing an internal RFID system in such a cabinet can pose challenges. Where internal articles can have random placement within the cabinet, the RFID system must be such that there are no "dead zones" that the RFID system is unable to reach. In general, dead zones are areas in which the level of coupling between an RFID reader antenna and an RFID tag is not adequate for the system to perform a successful read of the tag. The existence of such dead zones may be caused by orientations in which the tag and the reader antennae are in orthogonal planes. Thus, articles placed in dead zones may not be detected thereby resulting in inaccurate tracking of tagged articles.

Often in the medical field, there is a need to read a large number of tags attached to articles in such an enclosure, and as mentioned above, such enclosures have limited access due to security reasons. The physical dimension of the enclosure may need to vary to accommodate a large number of articles or articles of different sizes and shapes. In order to obtain an accurate identification and count of such closely-located medical articles or devices, a robust electromagnetic energy field must be provided at the appropriate frequency within the enclosure to surround all such stored articles and devices to be sure that their tags are all are activated and read. Such medical devices may have the RFID tags attached to the outside of their containers and may be stored in various orientations with the RFID tag (and associated antenna) pointed upwards, sideways, downward, or at some other angle in a random pattern.

Generating such a robust EM energy field is not an easy task. Where the enclosure has a size that is resonant at the frequency of operation, it can be easier to generate a robust EM field since a resonant standing wave may be generated within the enclosure. However, in the RFID field the usable frequencies of operation are strictly controlled and are limited. It has been found that enclosures are desired for the storage of certain articles that do not have a resonant frequency that matches one of the allowed RFID frequencies. Thus, a robust EM field must be established in another way.

Additionally, where EM energy is introduced to such an enclosure for reading the RFID tags within, efficient energy transfer is of importance. Under static conditions, the input or injection of EM energy into an enclosure can be maximized with a simple impedance matching circuit positioned between the conductor delivering the energy and the enclosure. As is well known to those of skill in the art, such impedance matching circuits or devices maximize the power transfer to the enclosure while minimizing the reflections of power from the enclosure. Where the enclosure impedance changes due to the introduction or removal of articles to or from the enclosure, a static impedance matching circuit may not provide optimum energy transfer into the enclosure. If the energy transfer and resulting RF field intensity within the enclosure were to fall below a threshold level, some or many of the tags on articles within the enclosure would not be activated to identify themselves, leaving an ineffective inventory system.

It is a goal of many health care facilities to keep the use of EM energy to a minimum, or at least contained. The use of high-power readers to locate and extract data from RFID tags is generally undesirable in health care facilities, although it may be acceptable in warehouses that are sparsely populated with workers, or in aircraft cargo holds. Radiating a broad beam of EM energy at a large area, where that EM energy may stray into adjacent, more sensitive areas, is undesirable. Efficiency in operating a reader to obtain the needed identification information from tags is an objective. In many cases where RFID tags are read, hand-held readers are used. Such readers transmit a relatively wide beam of energy to reach all RFID tags in a particular location. While the end result of activating each tag and reading it may be accomplished, the transmission of the energy is not controlled except by the aim of the user. Additionally, this is a manual system that will require the services of one or more individuals, which can also be undesirable in facilities where staff is limited Hence, those of skill in the art have recognized a need for a medication cabinet that provides both a refrigerated drawer and a non-refrigerated drawer to reduce costs and space requirements and accommodate various types of medications. A need has also been recognized for an RFID tag reader system in which the efficient use of energy is made to activate and read all RFID tags in an enclosed area. A further need for establishing a robust EM field in enclosures to activate and read tags disposed at random orientations has also been recognized. A further need has been recognized for an automated system to identify articles stored in a metal cabinet without the need to gain access to the cabinet. The present invention fulfills these needs and others.

SUMMARY OF THE INVENTION

Briefly and in general terms, the present invention is directed to a system for providing both refrigerated and non-refrigerated drawers in a single medication cabinet with the use of RFID to identify and track medical articles. In particular, there is provided a cabinet for storing medical articles, comprising a frame having a plurality of openings for receiving drawers, the frame providing an electrically conductive cage about a first opening to receive a first drawer, the cage having a front locate at the opening and a rear, a plurality of drawers, each of which is configured to be received by a respective opening and is movable into and out of the respective opening with the first drawer being configured to be received by the opening having the cage, a thermoelectric cooling ("TEC") device configured to provide cooling for a single drawer, a second opening adjacent the first opening having no cooling device, insulation disposed between the first and second openings configured to inhibit cooling from the thermoelectric cooling device from reaching the drawer of the second opening, and an RFID reader disposed within the cabinet and configured to read data from an RFID tag located within the cabinet.

In accordance with more detailed features, the TEC device is mounted to the frame such that the respective drawer moves toward it when the drawer is moved to the closed position and moves away from it when the drawer is moved to the open position. The respective TEC drawer includes a TEC device enclosure formed at a rear portion of the drawer, configured to receive the TEC device into the enclosure when the drawer is in the closed position, whereby the depth of the cabinet is reduced. The TEC device enclosure comprises a cooling diffuser configured to assist in circulating cooling equally throughout the drawer from the TEC device. Also, the drawer having the TEC device enclosure further includes partitions configured to separate medical articles from one another when stored in the drawer, the partitions also configured such that cooling from the TEC device is not inhibited from circulating equally throughout the drawer by the partitions.

In other detailed aspects, the RFID reader comprises an antenna that protrudes into the drawer, a drawer includes a TEC enclosure for receiving the TEC device when the drawer is in the closed position, the enclosure located so as to not interfere with the operation of the antenna in reading tagged articles located in the drawer. The first drawer is slidable into and out of the first opening of the cabinet, the drawer having a front panel that is electrically conductive and that contacts the electrically conductive cage at the first opening when the drawer is slid to a predetermined position within the cabinet. A portion of the first drawer is formed of electrically conductive material which is located at a position on the drawer such it comes into contact with the electrically conductive cage to thereby close an electrically conductive cage about the drawer.

In yet another aspect in accordance with the invention, the RFID reader is configured and positioned within the cabinet to force a resonance in a drawer to result in a robust electromagnetic field for reading tagged medical articles stored in the drawer.

Other detailed aspects include the first drawer being non-electrically conductive except for the portion of the drawer that contacts the cage to close the cage about the drawer. And further, a temperature sensor is disposed so as to measure the temperature in a drawer.

The features and advantages of the invention will be more readily understood from the following detailed description that should be read in conjunction with the accompanying drawings.

DETAILED DESCRIPTION OF THE PREFERRED EMBODIMENTS

Figure 1:
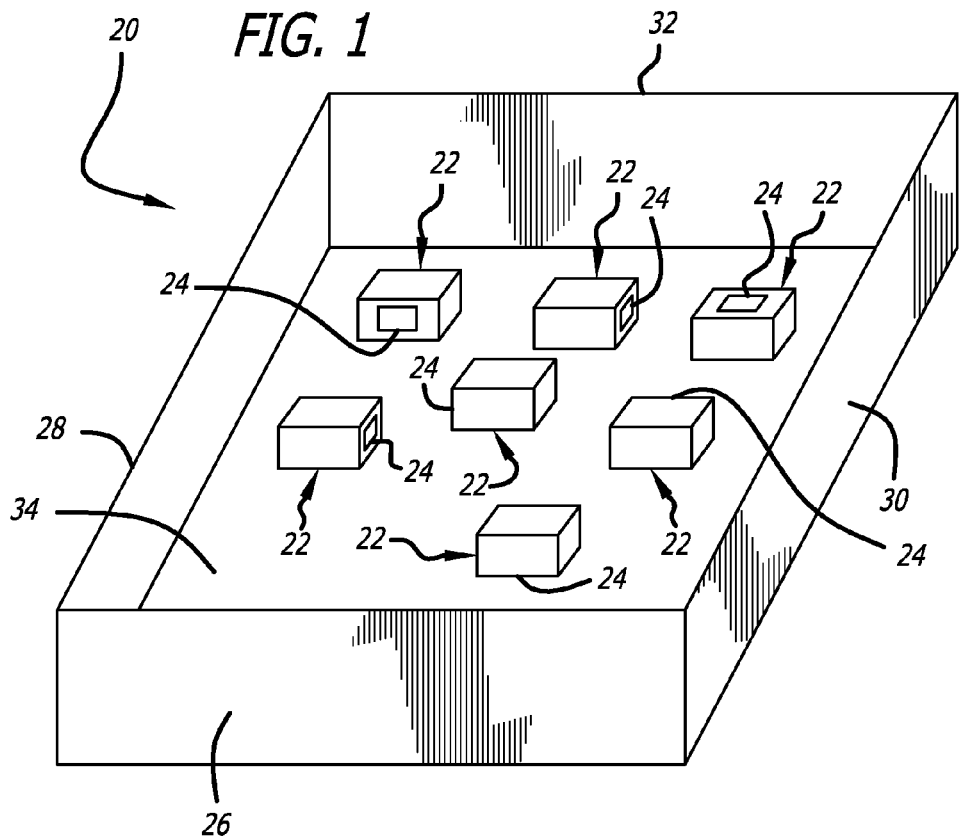
FIG. 1 is a schematic diagram of a drawer that may be positioned within a medical dispensing cabinet, showing the storage of a plurality of medical articles randomly positioned in the drawer, each of those articles having an integral RFID tag oriented randomly.

Referring now in more detail to the exemplary drawings for purposes of illustrating embodiments of the invention, wherein like reference numerals designate corresponding or like elements among the several views, there is shown in FIG. 1 a schematic representation of a partial enclosure 20 in which a plurality of medical articles 22 are stored, each with a respective RFID tag 24 that has a unique identification number. The partial enclosure may comprise a drawer having a front 26, a left side 28, a right side 30, a rear 32, and a bottom 34. These articles are randomly distributed in the drawer with the RFID tags facing in various and random directions.

As used in regard to the embodiments herein, "reader" and "interrogator" refer to a device that may read or write/read. The data capture device is always referred to as a reader or an interrogator regardless of whether it can only read or is also capable of writing. A reader typically contains a radio frequency module (a transmitter and a receiver, sometimes referred to as a "transceiver"), a control unit and a coupling element (such as an antenna or antennae) to the RFID tag. Additionally, many readers include an interface for forwarding data elsewhere, such as an RS-232 interface. The reader, when transmitting, has an interrogation zone within which an RFID tag will be activated. When within the interrogation zone, the RFID tag will draw its power from the electrical/magnetic field created in the interrogation zone by the reader. In a sequential RFID system (SEQ), the interrogation field is switched off at regular intervals. The RFID tag is programmed to recognize these "off" gaps and they are used by the tag to send data, such as the tag's unique identification number. In some systems, the tag's data record contains a unique serial number that is incorporated when the tag is manufactured and which cannot be changed. This number may be associated in a data base with a particular article when the tag is attached to that article. Thus, determining the location of the tag will then result in determining the location of the article to which it is attached. In other systems, the RFID tag may contain more information about the article to which it is attached, such as the name or identification of the article, its expiration date, it dose, the patient name, and other information. The RFID tag may also be writable so that it can be updated.

As used in regard to the embodiments herein, "tag" is meant to refer to an RFID transponder. Such tags typically have a coupling element, such as an antenna, and an electronic microchip. The microchip includes data storage, also referred to as memory.

Figure 2:
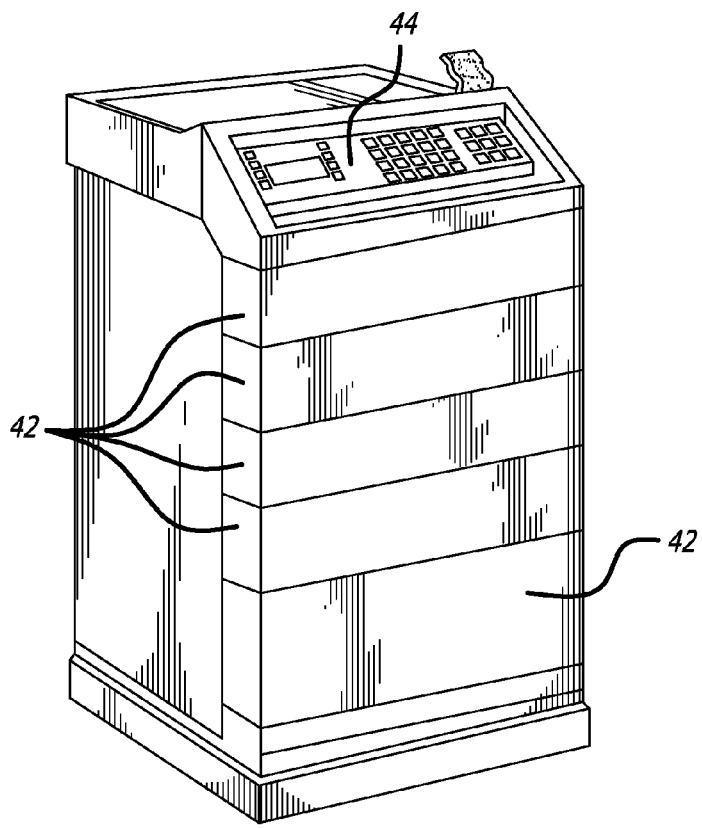
FIG. 2 is a perspective view of a medication dispensing cabinet having five drawers, one of which is similar to the schematic view of FIG. 1, the cabinet also having an integral computer for controlling access to the cabinet and performing inventory tracking by periodically reading any RFID tags placed on articles stored within the cabinet, and for reporting the identified articles to a remote computer.

FIG. 2 presents a representative medical dispensing cabinet 40 comprising a plurality of movable drawers 42. In this embodiment, there are five drawers that slide outwardly from the cabinet so that access is provided to the contents of the drawers. FIG. 1 is a schematic diagram of a representative drawer that may be positioned within the cabinet of FIG. 2 for sliding outward to provide access to the drawer's contents and for sliding inward into the cabinet to secure the drawer's contents. The cabinet also comprises an integral computer 44 that may be used to control access to the drawers and to generate data concerning access and contents, and to communicate with other systems. In this embodiment, the computer generates data concerning the number and type of articles in the drawers, the names of the patients for whom they have been prescribed, the prescribed medications and their prescribed administration dates and times, as well as other information. In a simpler system, the computer may simply receive unique identification numbers from stored articles and pass those identification numbers to an inventory control computer that has access to a data base for matching the identification numbers to article descriptions.

Such a cabinet may be located at a nursing station on a particular floor of a health care institution and may contain the prescriptions for the patients of that floor. As prescriptions are prepared for the patients of that floor, they are delivered and placed into the cabinet 40. They are logged into the integral computer 44, which may notify the pharmacy of their receipt. A drawer may also contain non-prescription medical supplies or articles for dispensing to the patients as determined by the nursing staff. At the appropriate time, a nurse would access the drawer in which the medical articles are stored through the use of the computer 44, remove a particular patient's prescriptions and any needed non-prescription articles, and then close the drawer so that it is secured. In order to access the cabinet, the nurse may need to provide various information and may need a secure access code. The drawers 42 may be locked or unlocked as conditions require.

The computer 44 in some cases may be in communication with other facilities of the institution. For example, the computer 44 may notify the pharmacy of the health care institution that a patient's prescription has been removed from the cabinet for administration at a particular day and time. The computer may also notify the finance department of the health care institution of the removal of prescriptions and other medical articles for administration to a particular patient. This medication may then be applied to the patient's account. Further, the computer 44 may communicate to administration for the purpose of updating a patient's Medication Administration Record (MAR), or e-MAR. The medication cabinet 40 computer 44 may be wirelessly connected to other computers of the health care institution or may have a wired connection. The cabinet may be mounted on wheels and may be moved about as needed or may be stationary and unable to move.

Figure 3:
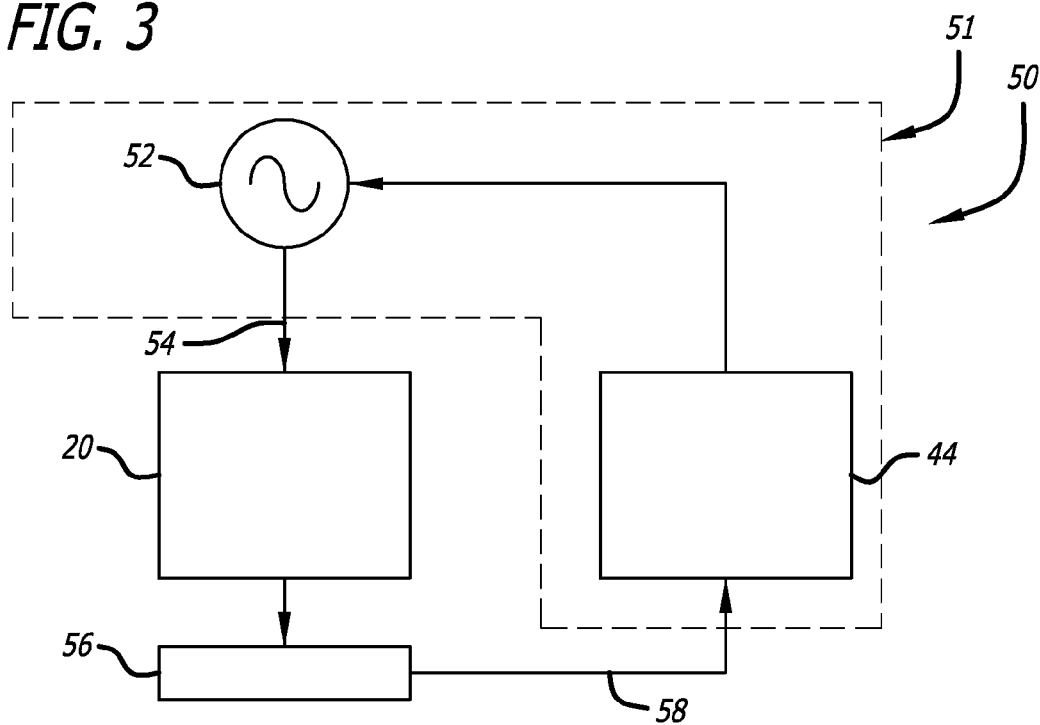
FIG. 3 is a block and flow diagram showing an embodiment in which an RFID reader transmits activating EM energy into a drawer containing RFID tags with a single transmitting antenna, receives the data output from the activated RFID tags with a single receiving antenna, a computer controlling the transmission of activating energy and receiving the data from the activated RFID tags for processing.
Figure 4:
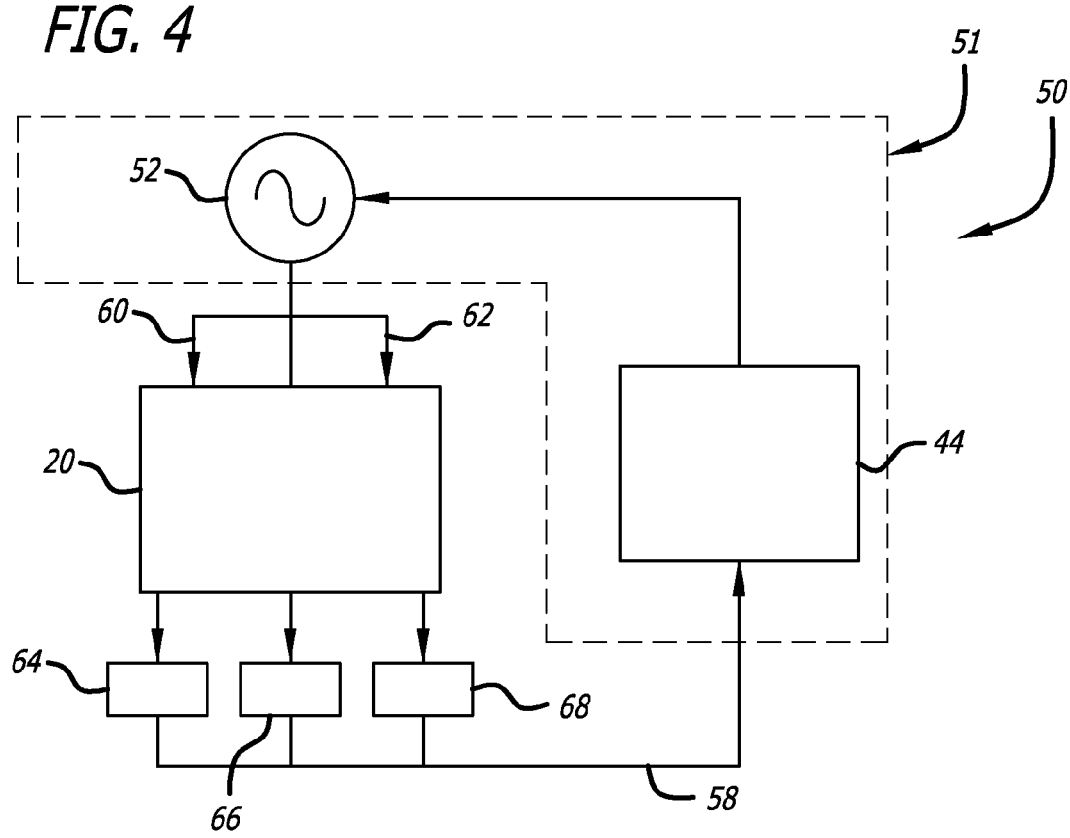
FIG. 4 is a block and flow diagram similar to FIG. 3 showing an embodiment in which an RFID reader transmits activating EM energy into a drawer containing RFID tags with two transmitting antennae, receives the data output from the activated RFID tags with three receiving antennae, and as in FIG. 3, a computer controlling the transmission of activating energy and receiving the data from the activated RFID tags for processing.

Systems that use RFID tags often employ an RFID reader in communication with one or more host computing systems that act as depositories to store, process, and share data collected by the RFID reader. Turning now to FIGS. 3 and 4, a system and method 50 for tracking articles are shown in which a drawer 20 of the cabinet 40 of FIG. 2 is monitored to obtain data from RFID tags disposed with articles in that drawer. As mentioned above, a robust field of EM energy needs to be established in the storage site so that the RFID tags mounted to the various stored articles will be activated, regardless of their orientation.

In FIGS. 3 and 4, the tracking system 50 is shown for identifying articles in an enclosure and comprises a transmitter 52 of EM energy as part of an RFID reader. The transmitter 52 has a particular frequency, such as 915 MHz, for transmitting EM energy into a drawer 20 by means of a transmitting antenna 54. The transmitter 52 is configured to transmit the necessary RFID EM energy and any necessary timing pulses and data into the enclosure 20 in which the RFID tags are disposed. In this case, the enclosure is a drawer 20. The computer 44 of an RFID reader 51 controls the EM transmitter 52 to cycle between a transmit period and a non-transmit, or off, period. During the transmit period, the transmitted EM energy at or above a threshold intensity level surrounds the RFID tags in the drawer thereby activating them. The transmitter 52 is then switched to the off period during which the RFID tags respond with their respective stored data.

The embodiment of FIG. 3 comprises a single transmitting probe antenna 54 and a single receiving antenna 56 oriented in such a manner so as to optimally read the data transmitted by the activated RFID tags located inside the drawer 20. The single receiving antenna 56 is communicatively coupled to the computer 44 of the reader 50 located on the outside of the drawer 20 or on the inner bottom of the drawer. Other mounting locations are possible. Coaxial cables 58 or other suitable signal links can be used to couple the receiving antenna 56 to the computer 44. A wireless link may be used in a different embodiment. Although not shown in the figures, those skilled in the art will recognize that various additional circuits and devices are used to separate the digital data from the RF energy, for use by the computer. Such circuits and devices have not been shown in FIGS. 3 and 4 to avoid unneeded complexity in the drawing.

The embodiment of FIG. 4 is similar to the embodiment of FIG. 3 but instead uses two transmitting probe antennae 60 and 62 and three receiving antennae 64, 66, and 68. The configuration and the number of transmitting probe antennae and receiving antennae to be used for a system may vary based at least in part on the size of the enclosure 20, the frequency of operation, the relationship between the operation frequency and the natural resonance frequency of the enclosure, and the expected number of RFID tags to be placed in it, so that all of the RFID tags inside the enclosure can be reliably activated and read. The location and number of RFID reader components can be dependent on the particular application. For example, fewer components may be required for enclosures having a relatively small size, while additional components, such as shown in FIG. 4, may be needed for larger enclosures. Although shown in block form in FIGS. 3 and 4, it should be recognized that each receiving antenna 56, 64, 66, and 68 of the system 50 may comprise a sub-array in a different embodiment.

The transmit antennae (54, 60, and 62) and the receive antennae (56, 64, 66, and 68) may take different forms. In one embodiment as is discussed in more detail below, a plurality of "patch" or microstrip antennae were used as the reader receiving antennae and were located at positions adjacent various portions of the bottom of the drawer while the transmit antennae were wire probes located at positions adjacent portions of the top of the drawer. It should be noted that in the embodiments of FIGS. 3 and 4, the RFID reader 50 may be permanently mounted in the same cabinet at a strategic position in relation to the drawer 20.

One solution for reliably interrogating densely packed or randomly oriented RFID tags in an enclosure is to treat the enclosure as a resonant cavity. Establishing a resonance within the cavity enclosure can result in a robust electromagnetic field capable of activating all RFID tags in the enclosure. This can be performed by building an enclosure out of electrically conductive walls and exciting the metallic enclosure, or cavity, using a probe or probes to excite transverse electric (TE) or transverse magnetic (TM) fields in the cavity at the natural frequency of resonance of the cavity. This technique will work if the cavity dimensions can be specifically chosen to set up the resonance at the frequency of operation or if the frequency of operation can be chosen for the specific enclosure size. Since there are limited frequency bands available for use in RFID applications, varying the RFID frequency is not an option for many applications. Conversely, requiring a specific set of physical dimensions for the enclosure so that the natural resonant frequency of the enclosure will equal the available RFID tag activating frequency will restrict the use of this technique for applications where the enclosure needs to be of a specific size. This latter approach is not practical in view of the many different sizes, shapes, and quantities of medical articles that must be stored.

Figure 5:
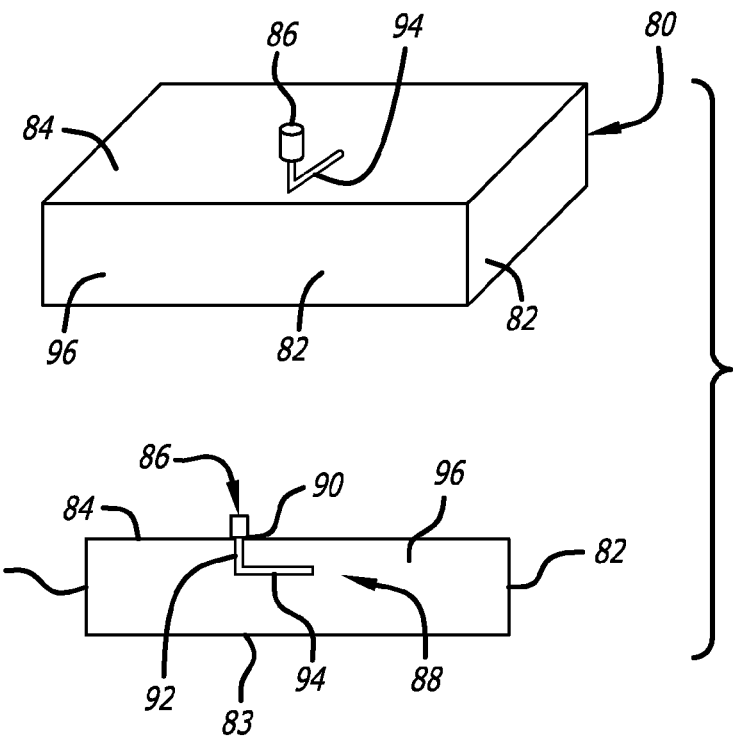
FIG. 5 shows an enclosure with a single probe and a connector, the probe being configured to inject EM energy into the enclosure and excite a TE mode.

Referring now to FIG. 5, a rectangular enclosure 80 is provided that may be formed as part of a medical cabinet, such as the cabinet shown in FIG. 2. It may be embodied as a frame disposed about a non-metallic drawer in such a cabinet. The enclosure 80 is formed of metallic or metallized walls 82, floor 83, and ceiling 84 surfaces, all of which are electrically conductive. All of the walls 82, floor 83, and ceiling 84 may also be referred to herein as "walls" of the enclosure. FIG. 5 also shows the use of an energy coupling or probe 86 located at he top surface 84 of the enclosure 80. In this embodiment, the probe takes the form of a capacitor probe 88 in that the probe 88 has a first portion 94 that proceeds axially through a hole 90 in the ceiling 84 of the enclosure. The purpose of the coupling is to efficiently transfer the energy from the source 52 (see FIGS. 3 and 4) to the interior 96 of the enclosure 80. The size and the position of the probe are selected for effective coupling and the probe is placed in a region of maximum field intensity. In FIG. 5, a $TE_{01}$ mode is established through the use of capacitive coupling. The length and distance of the bent portion 94 of the probe 88 affects the potential difference between the probe and the enclosure 80.

Figure 6:
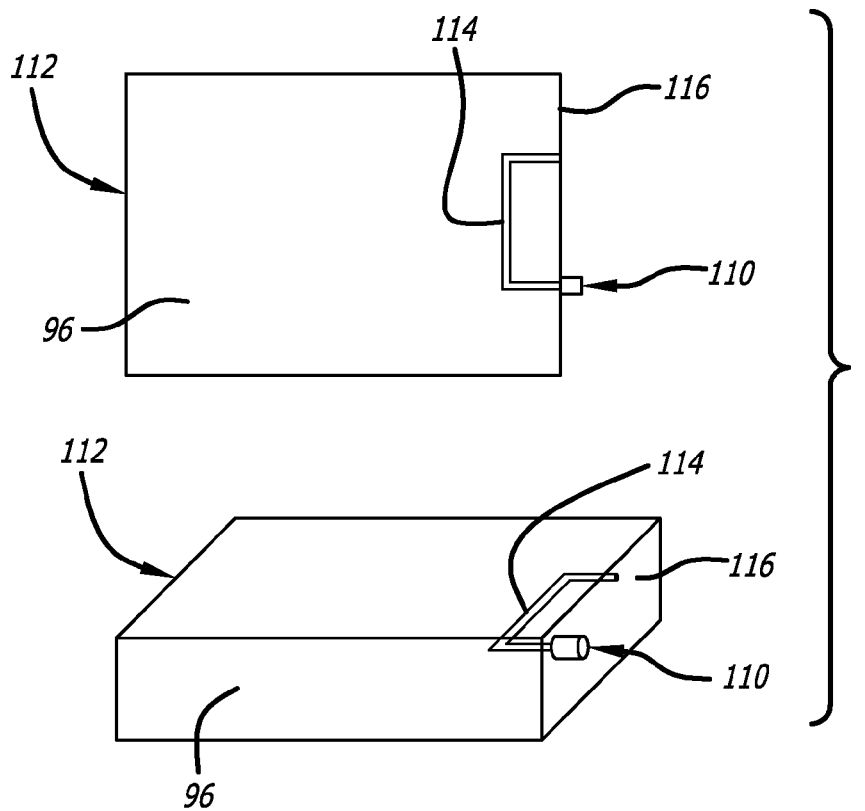
FIG. 6 shows an enclosure with a single probe and a connector, the probe being configured to inject EM energy into the enclosure and excite a TM mode.

Similarly, FIG. 6 presents an inductive coupling 110 of the external energy to an enclosure 112. The coupling takes the form of a loop probe 114 mounted through a side wall 116 of the enclosure. The purpose of this probe is to establish a $TM_{01}$ mode in the enclosure.

Figure 7:
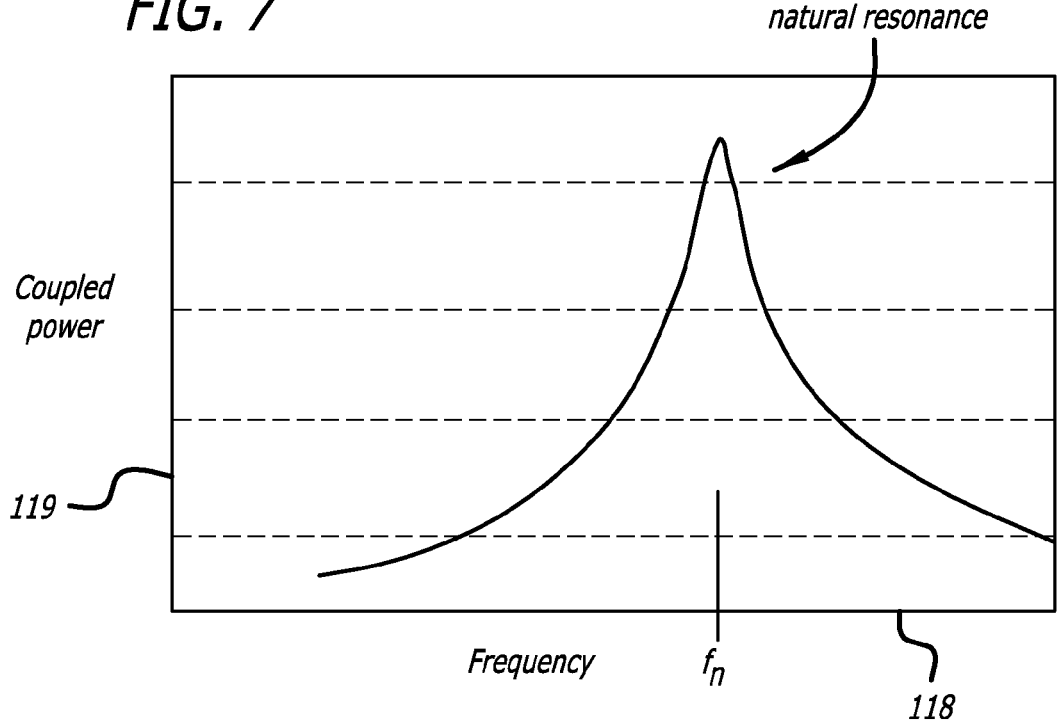
FIG. 7 shows a plot of coupled power in an enclosure as a function of frequency for a resonant enclosure where $F_n$ is the natural resonance frequency of the enclosure.

The rectangular enclosures 80 and 112 shown in FIGS. 5 and 6 each have a natural frequency of resonance $f_n$, shown in FIG. 7 and indicated on the abscissa axis 118 of the graph by $f_n$. This is the frequency at which the coupled power in the enclosure is the highest, as shown on the ordinate axis 119 of the graph. If the injected energy to the enclosure does not match the $f_n$ frequency, the coupled power will not benefit from the resonance phenomenon of the enclosure. In cases where the frequency of operation cannot be changed, and is other than $f_n$, and the size of the enclosure cannot be changed to obtain an $f_n$ that is equal to the operating frequency, another power coupling apparatus and method must be used. In accordance with aspects of the invention, an apparatus and method are provided to result in a forced resonance $f_f$ within the enclosure to obtain a standing wave within the enclosure with constructive interference. Such a standing wave will establish a robust energy field within the enclosure strong enough to activate all RFID tags residing therein.

Figure 8:
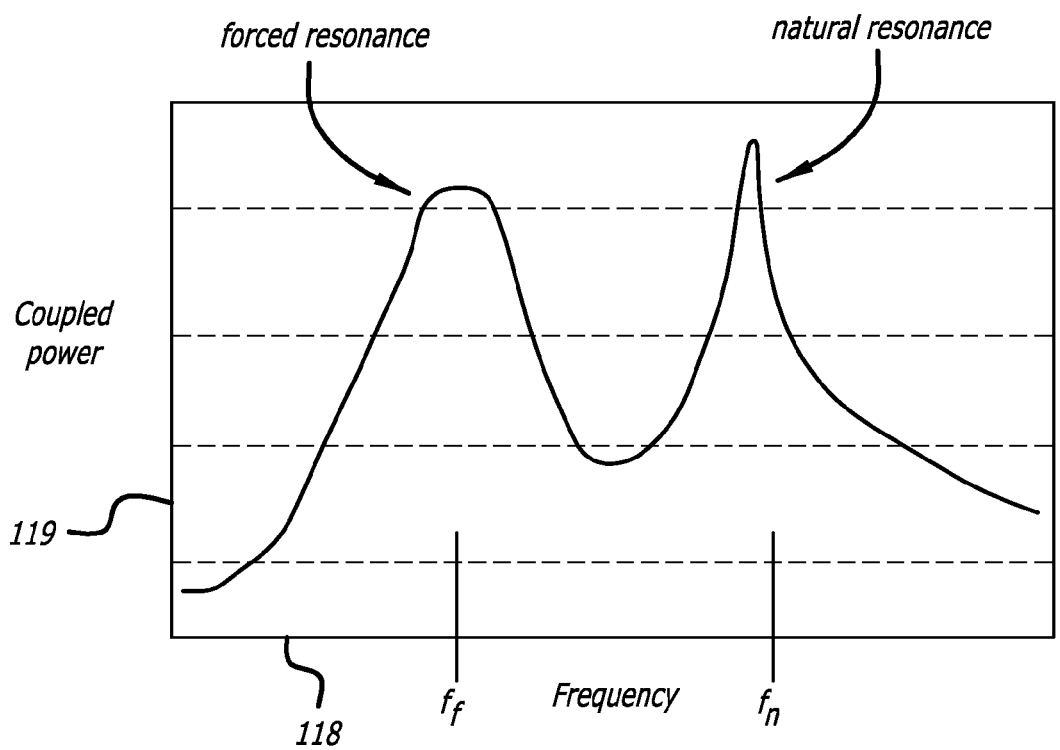
FIG. 8 shows a plot of coupled power (ordinate axis) in an enclosure as a function of frequency (abscissa axis), where $f_f$ is a forced resonance frequency, or otherwise referred to as a frequency that is not equal to the resonant frequency of the enclosure, and $f_n$ is the natural resonant frequency of the enclosure, showing the establishment of a robust field of coupled power in the enclosure at the $f_f$ frequency.

When an EM wave that is resonant with the enclosure enters, it bounces back and forth within the enclosure with low loss. As more wave energy enters the enclosure, it combines with and reinforces the standing wave, increasing its intensity (constructive interference). Resonation occurs at a specific frequency because the dimensions of the cavity are an integral multiple of the wavelength at the resonance frequency. In the present case where the injected energy is not at the natural resonance frequency $f_n$ of the enclosure, a solution in accordance with aspects of the invention is to set up a "forced resonance" in an enclosure. This forced resonance is different from the natural resonance of the enclosure in that the physical dimensions of the enclosure are not equal to an integral multiple of the wavelength of the excitation energy, as is the case with a resonant cavity. A forced resonance can be achieved by determining a probe position, along with the probe length to allow for energy to be injected into the cavity such that constructive interference results and a standing wave is established. The energy injected into the enclosure in this case will set up an oscillatory field region within the cavity, but will be different from a standing wave that would be present at the natural resonance frequency $f_n$ of a resonant cavity. The EM field excited from this forced resonance will be different than the field structure found at the natural resonance of a resonant cavity, but with proper probe placement of a probe, a robust EM field can nevertheless be established in an enclosure for RFID tag interrogation. Such is shown in FIG. 8 where it will be noted that the curve for the forced resonance $f_f$ coupled power is close to that of the natural resonance $f_n$.

Figure 9:
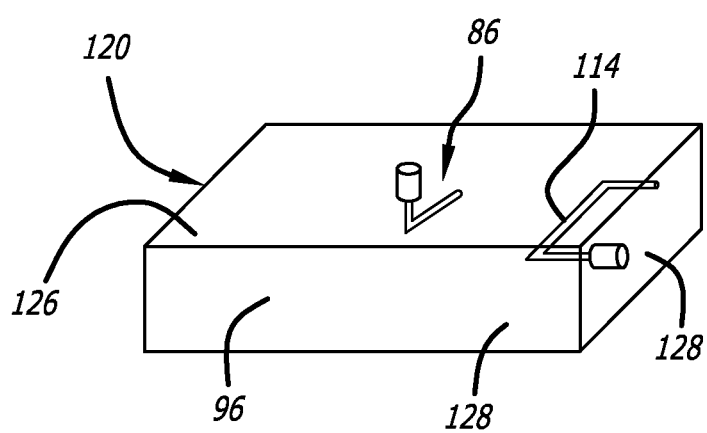
FIG. 9 shows an enclosure with two probes each with a connector for injecting EM energy into the enclosure, one probe being a TM probe and the other being a TE probe.

Turning now to FIG. 9, an enclosure 120 having two energy injection probes is provided. The first probe 86 is capacitively coupled to the enclosure 120 in accordance with FIG. 5 to establish a $TE_{01}$ mode. The second probe 114 is inductively coupled to the enclosure 120 in accordance with FIG. 6 to establish a $TM_{01}$ mode. These two probes are both coupled to the enclosure to inject energy at a frequency $f_f$ that is other than the natural resonance frequency $f_n$ of the enclosure. The placement of these probes in relation to the ceiling 126 and walls 128 of the enclosure will result in a forced resonance within the enclosure 120 that optimally couples the energy to the enclosure and establishes a robust EM field within the enclosure for reading RFID tags that may be located therein. The placement of these probes in relation to the walls of the enclosure, in accordance with aspects of the invention, result in the forced resonance curve $f_f$ shown in FIG. 8.

Figure 10:
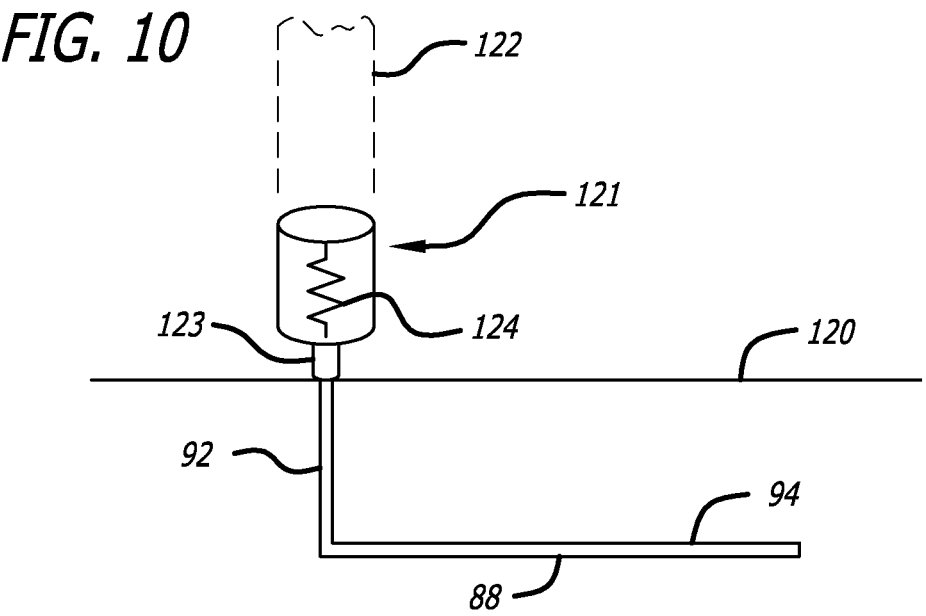
FIG. 10 shows a probe, a connector, and an attenuator that is used to improve the impedance match between the probe and the enclosure.
Figure 11:
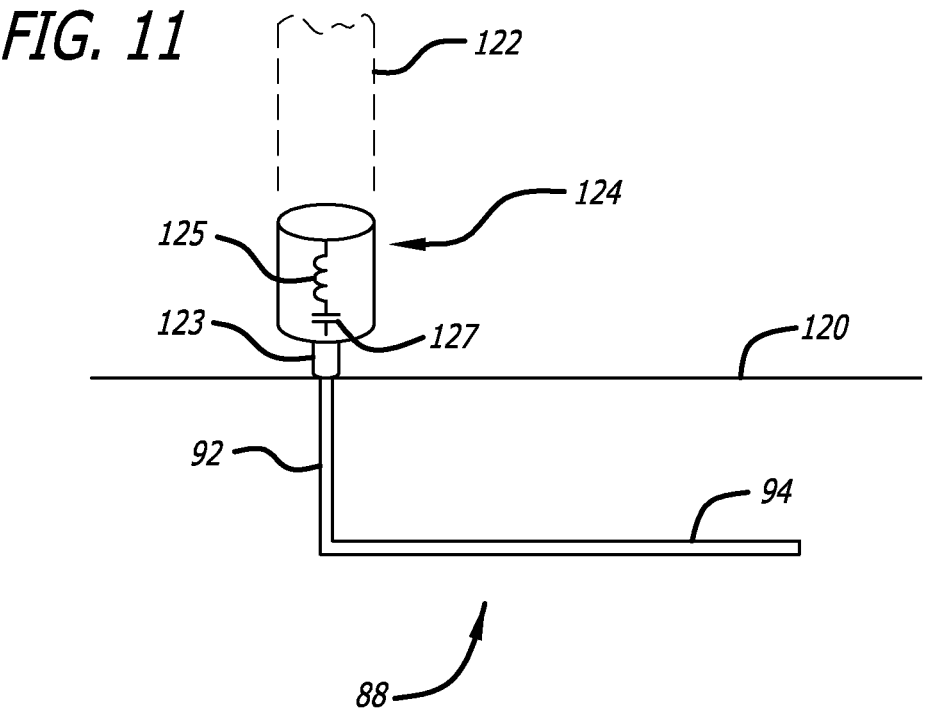
FIG. 11 shows a probe, a connector, and a passive matching circuit that is used to improve the impedance match between the probe and enclosure.

Referring briefly to FIG. 10, an impedance matching circuit 121 is shown that functions to match the impedance of a source of energy 122 to the enclosure 120. The impedance matching circuit is located between the coaxial cable 122 that feeds activating energy to the enclosure 120 and the capacitively coupled probe 88 through a hole in the metallic ceiling 126 of the enclosure. While the hole is not shown in the drawing of FIG. 10, the insulator 123 that electrically insulates the probe from the metallic ceiling is shown. In this case, the matching circuit 121 consists of only a resistive attenuator 124 used to reduce reflections of energy by the enclosure 120. However, as will be appreciated by those of skill in the art, capacitive and inductive components are likely to exist in the enclosure and in the coupling 88. FIG. 11 on the other hand presents an impedance matching circuit 124 having passive reactive components for use in matching the impedance of the coaxial cable/energy source 122 and the enclosure 120. In this exemplary impedance matching circuit 124, an inductive component 125 and a capacitive component 127 are connected in series, although other configurations, including the addition of a resistive component and other connection configurations, are possible.

Passive components such as resistors, inductors, and capacitors shown in FIGS. 10 and 11 can be used to form matching circuits to match the impedances of the energy source and the enclosure. This will aid in coupling power into the enclosure. However, the passive matching circuit will improve the impedance match for a specific enclosure loading, such as an empty enclosure, partially loaded, or fully loaded enclosure. But as the enclosure contents are varied, the impedance match may not be optimized due to the variation in contents in the enclosure causing the impedance properties of the enclosure to change.

Figure 12:
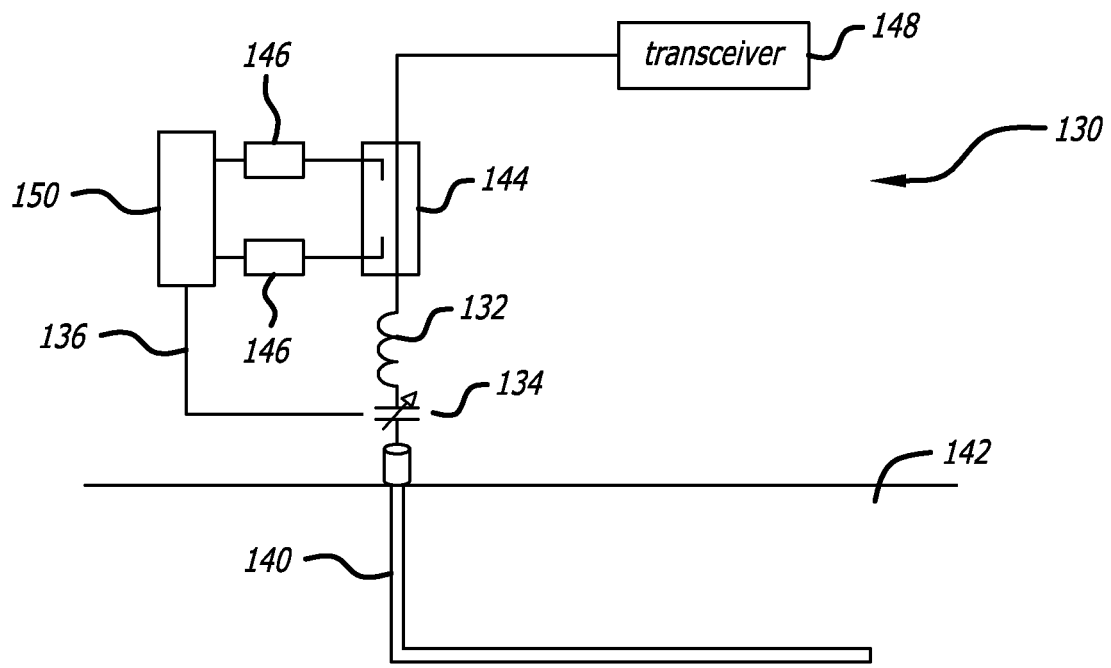
FIG. 12 shows an active matching circuit connected between a probe located in an enclosure and a transceiver, the active matching circuit comprising a tunable capacitor, a dual-directional coupler, multiple power sensors, and a comparator used to provide a closed-loop, variable matching circuit to improve the impedance match between the probe and the enclosure.

This non-optimal impedance match caused by variation in enclosure loading can be overcome by the use of an active impedance matching circuit which utilizes a closed loop sensing circuit to monitor forward and reflected power. Referring now to FIG. 12, an active matching circuit 130 is provided that comprises one or several fixed value passive components such as inductors 132, capacitors 134, or resistors (not shown). In addition, one or several variable reactance devices, such as a tunable capacitor 134, are incorporated into the circuit; these tunable devices making this an active impedance matching circuit. The tunable capacitor 134 can take the form of a varactor diode, switched capacitor assembly, MEMS capacitor, or BST (Barium Strontium Titanate) capacitor. A control voltage is applied to the tunable capacitor 134 and varied to vary the capacitance provide by the device. The tunable capacitor 134 provides the capability to actively change the impedance match between the probe 140 and the enclosure 142.

To complete the active matching circuit, a dual directional coupler 144 along with two power sensors 146 can be incorporated. The dual directional coupler 144 and the power sensors 146 provide the ability to sense forward and reflected power between the RFID transceiver 148 and the active matching circuit 130 and enclosure 142. Continuous monitoring of the ratio of forward and reflected power by a comparator 150 provides a metric to use to adjust the tunable capacitor 134 to keep the probe 140 impedance matched to the enclosure 142. An ability to continuously monitor and improve the impedance match as the contents of the enclosure are varied is provided with the active matching circuit 130.

Figure 13:
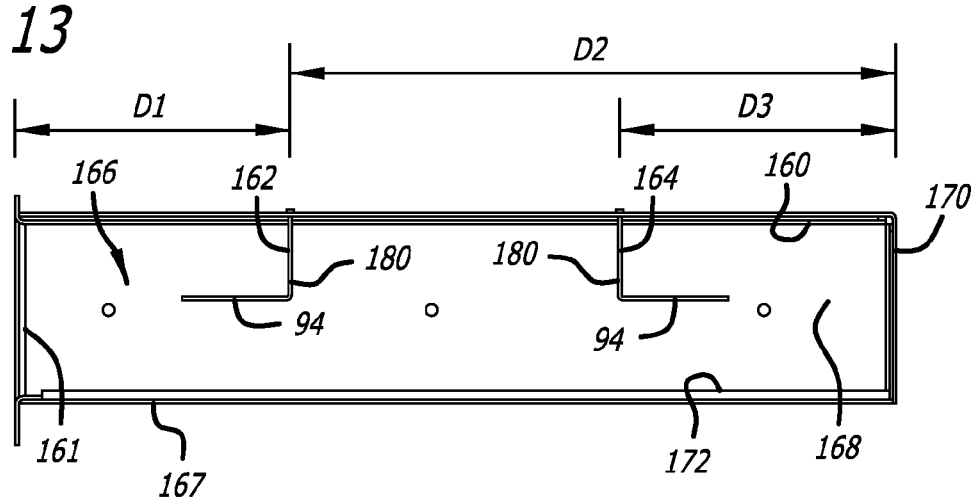
FIG. 13 provides a side cross-sectional view of the cabinet of FIG. 2 at the location of a drawer with the drawer removed for clarity, showing the placement of two probe antennae in a "ceiling mount" configuration for establishing a robust EM field in the drawer when it is in place in the cabinet in the closed position.

Referring now to the side cross-sectional view of FIG. 13, two ceiling-mounted 160 probe antennae 162 and 164 are shown mounted within an enclosure, which may also be referred to herein as a cavity 166, which in this embodiment, operates as a Faraday cage. As shown, the Faraday cage 166 comprises walls (one of which is shown) 168, a back 170, a floor 172, a ceiling 160, and a front 161 (only the position of the front wall is shown). All surfaces forming the cavity are electrically conductive, are electrically connected with one another, and are structurally formed to be able to conduct the frequency of energy $f_f$ injected by the two probes 162 and 164. In this embodiment, the cavity 166 is constructed as a metal frame 167 that may form a part of a medical supply cabinet similar to that shown in FIG. 2. Into that metal frame may be mounted a slidable drawer. The slidable drawer in this embodiment is formed of electrically inert material, that is, it is not electrically conductive, except for the front. When the drawer is slid into the cabinet to a closed configuration, the electrically conductive front panel of the drawer comes into electrical contact with another part or parts of the metallic frame 167 thereby forming the front wall 161 of the Faraday cage 167.

The amount of penetration or retention into the cavity by the central conductor 180 of each probe is selected so as to achieve optimum coupling. The length of the bent portion 94 of the probe is selected to result in better impedance matching. The position of the probe in relation to the walls of the cavity is selected to create a standing wave in the cavity. In this embodiment, the probe antennae 162 and 164 have been located at a particular distance D1 and D3 from respective front 161 and back 170 walls. These probe antennae, in accordance with one aspect of the invention, are only activated sequentially after the other probe has become inactivated. It has been found that this configuration results in a standing wave where the injected energy waves are in phase so that constructive interference results.

Figure 14:
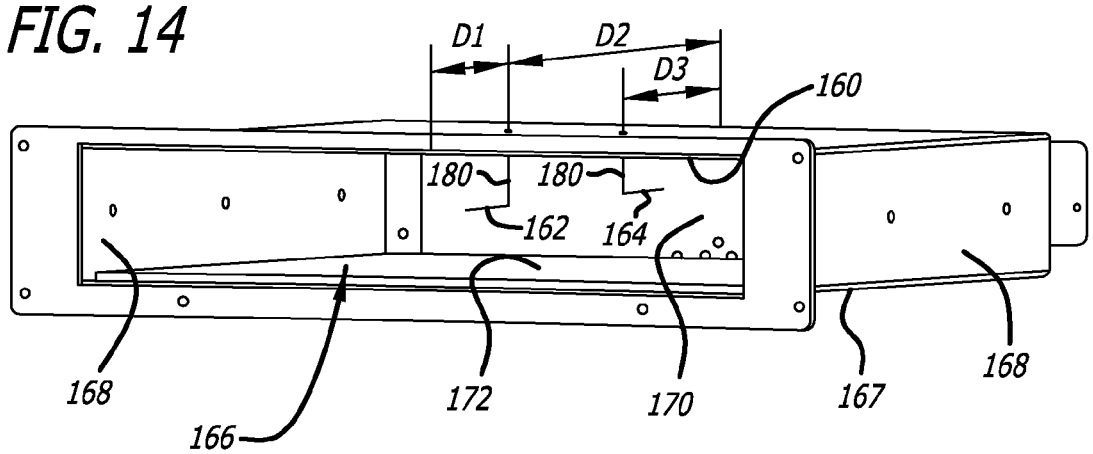
FIG. 14 is a perspective view of the metallic enclosure showing the probe configuration of FIG. 13 again showing the two probe antennae for establishing a robust EM field in a drawer to be inserted.

FIG. 14 is a front perspective view of the probe configuration of FIG. 13 again showing the two probe antennae 162 and 164 located in a Faraday-type enclosure 166 for establishing a robust EM field in an article storage drawer to be inserted. It should be noted again that the Faraday cavity 166 is constructed as a metallic frame 167. In this figure, the cavity is incomplete in that the front surface of the "cage" is missing. In one embodiment, this front surface is provided by an electrically conductive front panel of a slidable drawer. When the drawer is slid into the cabinet, the front panel will make electrical contact with the other portions of the metallic frame 167 thereby completing the Faraday cage 166, although other portions of the drawer are plastic or are otherwise non-electrically conductive. In the embodiment discussed and shown herein, the two probe antennae 162 and 164 are both located along a centerline between the side walls 166 and 168 of the frame 166. The enclosure in one embodiment was 19.2 inches wide with the probe antennae spaced 9.6 inches from each side wall. This centered location between the two side walls was for convenience in the case of one embodiment. The probes may be placed elsewhere in another embodiment. In this embodiment, the spacing of the probes 162 and 164 from each other is of little significance since they are sequentially activated. Although not shown, two receiving antennae will also be placed into the Faraday cage 166 to receive response signals from the activated RFID tags residing within the cavity 166.

It will also be noted from reference to the figures that the probes each have a bent portion used for capacitive coupling with the ceiling 160 of the cavity, as is shown in FIG. 13. The front probe 162 is bent forward while the back probe 164 is bent rearward A purpose for this configuration was to obtain more spatial diversity and obtain better coverage by the EM field established in the drawer. Other arrangements may be possible to achieve a robust field within the cavity 166. Additionally two probes were used in the particular enclosure 166 so that better EM field coverage of the enclosure 166 would result.

Figure 15:
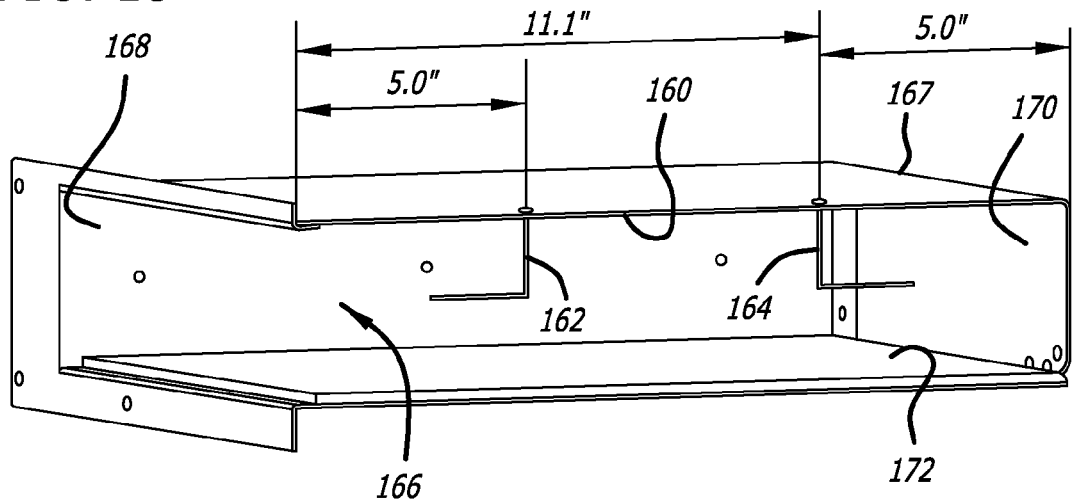
FIG. 15 is a cutaway perspective side view of the metallic enclosure or frame in which are mounted the dual probe antennae of FIGS. 13 and 14 with the drawer removed for clarity.

FIG. 15 is a cutaway perspective side view of the dual probe antennae 162 and 164 of FIGS. 13 and 14, also with the drawer removed for clarity. The front probe 162 is spaced from the left side wall by ½λ of the operating frequency $F_f$ as shown. It will be noted that the probes each have a bent portion used for capacitive coupling with the ceiling 160 of the enclosure 166 as shown in FIG. 13. The front probe 162 is bent forward for coupling with the more forward portion of the enclosure while the back probe 164 is bent rearward for coupling with the more rearward portion of the enclosure 166 to obtain more spatial diversity and obtain better coverage by the EM field in the drawer. Other arrangements may be possible to achieve a robust field and further spatial diversity and coverage within the enclosure.

Figure 16:
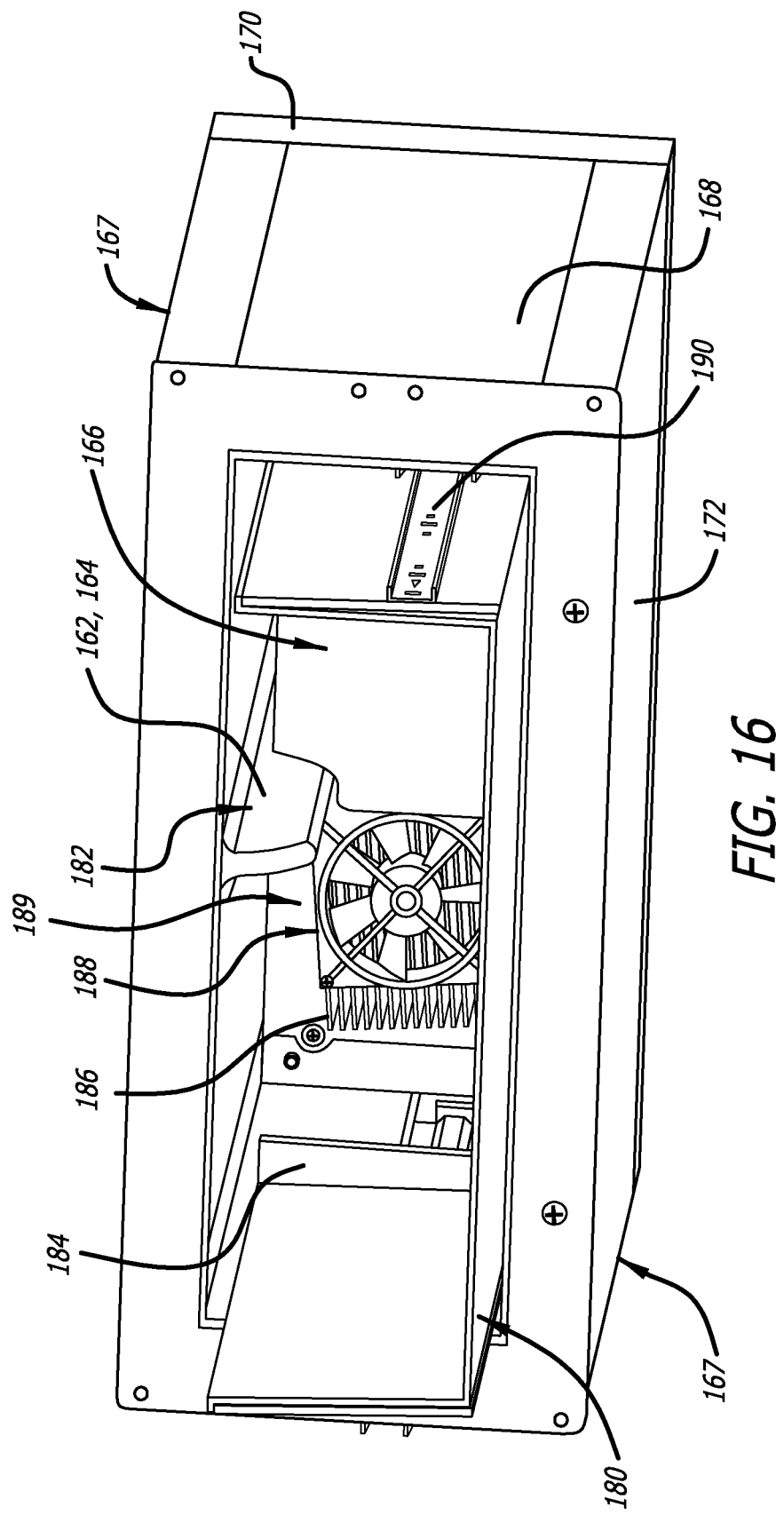
FIG. 16 is a frontal perspective view of the view of FIG. 14 with a cutaway plastic drawer in place in the metallic enclosure and further showing the dual ceiling mount probe antennae protected by an electromagnetically inert protective cover, and further showing cooling system components mounted at the back of the cabinet near the drawer's back, the drawing also showing a partial view of a drawer slide mechanism for ease in sliding the drawer between open and closed positions in the cabinet, the drawer front and rear panels having been cutaway in this view.

FIG. 16 is a frontal upward-looking perspective view of the frame 167 forming a Faraday cage 166 showing a portion of a drawer 180 that has been slidably mounted within the frame 167. The front metallic panel of the drawer has been removed so that its sliding operation can be more clearly seen. It will also be noted that the dual ceiling mount probe antennae 162 and 164 have been covered and protected by an electromagnetically inert protective cover 182. The drawer is formed of a non-metallic material, such as a plastic or other electromagnetic inert material having a low RF constant. The back 184 of the drawer has also been cut away so that a cooling system 189 comprising coils 186 and a fan 188 located in the back of the frame 167 can be seen. In this case, the drawer 180 is slidably mounted to the Faraday cage frame with metallic sliding hardware 190. The sliding hardware of the drawer is so near the side of the frame 167 of the enclosure 166 and may be in electrical contact with the metallic slide hardware of the side walls 168 of the enclosure that these metallic rails will have only a small effect on the EM field established within the enclosure.

Figure 17:
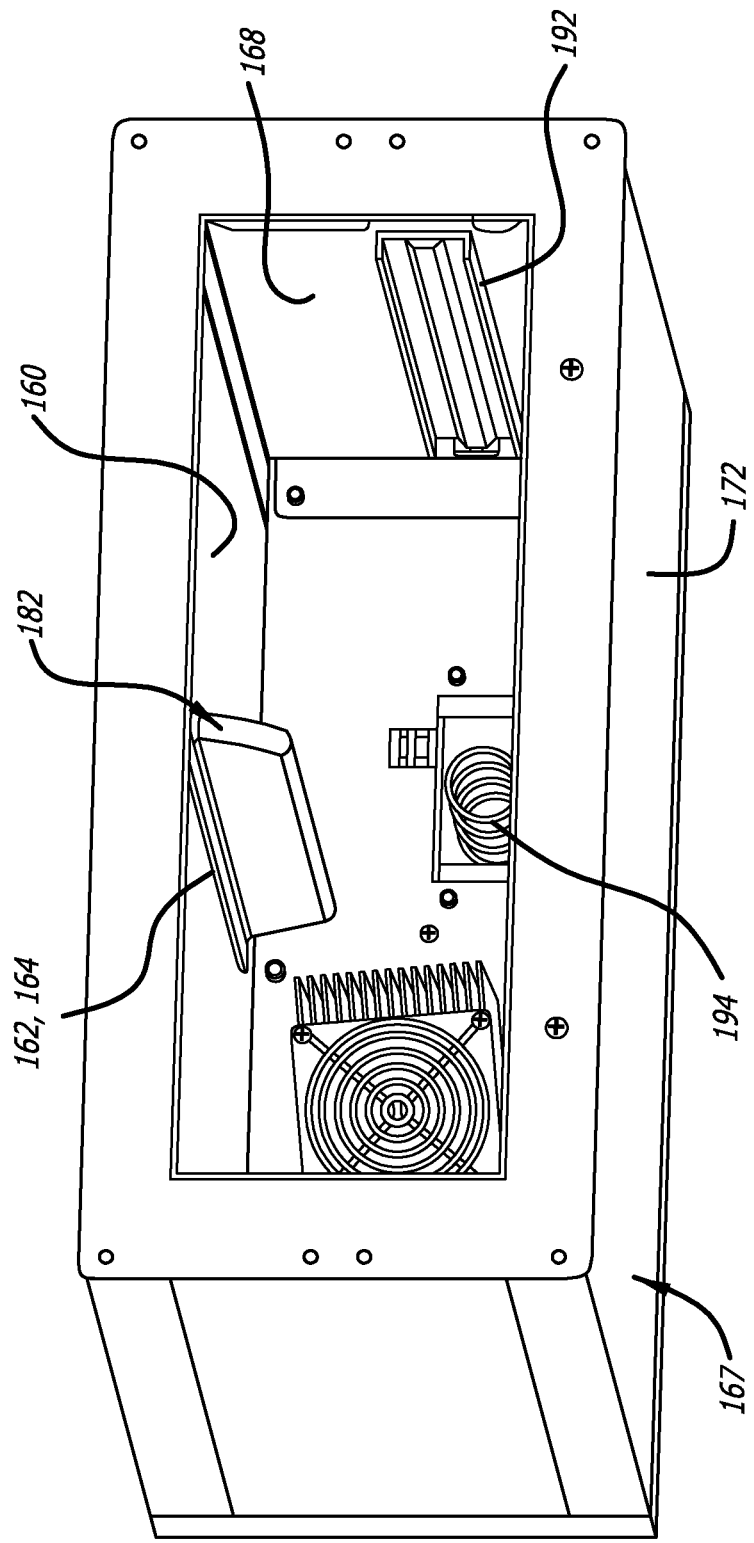
FIG. 17 is a frontal perspective view at the opposite angle from that of FIG. 16 with the plastic drawer completely removed showing the dual ceiling mount probe antennae protected by the EM inert protective cover mounted in the metallic enclosure, and further showing the cooling system components of FIG. 16 mounted at the back of the cabinet as a spring loading feature to automatically push the drawer to the open position when the drawer's latch is released, the figure also showing a mounting rail for receiving the slid of the drawer.

FIG. 17 is an upward looking, frontal perspective view at the opposite angle from that of FIG. 16; however, the drawer has been removed. The frame 167 in this embodiment includes a mounting rail 192 for receiving the slide of the drawer 180. In this embodiment, the mounting rail is formed of a metallic material; however, it is firmly attached to a side 168 of the Faraday cage and thus is in electrical continuity with the cage. The figure also shows a spring mechanism 194 used to assist in sliding the drawer outward so that access to the articles stored in the drawer may be gained. The spring is configured to automatically push the drawer outward when the drawer's latch is released.

Figure 18:
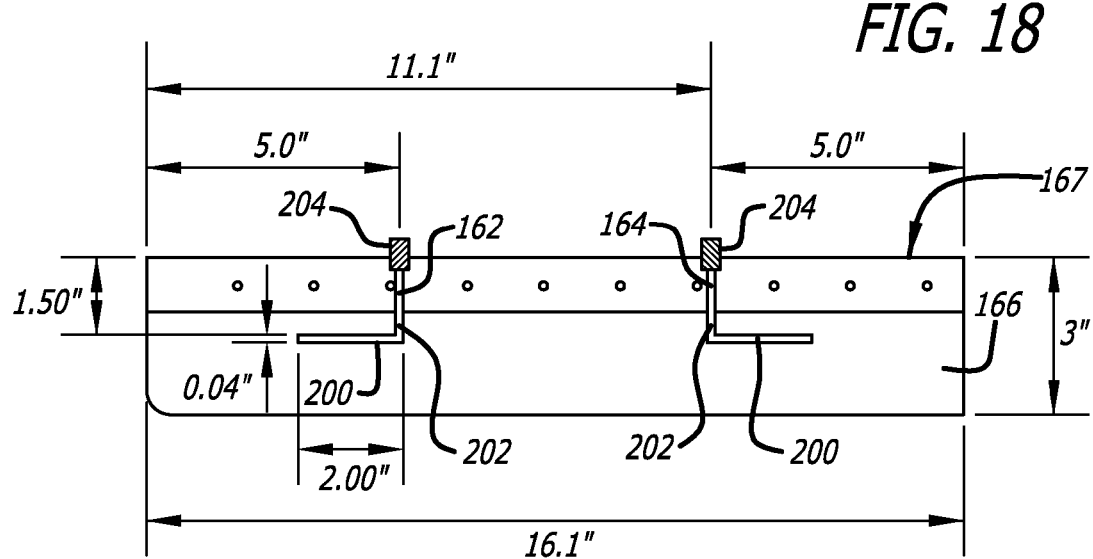
FIG. 18 is a schematic view with measurements in inches of the placement of two $TE_{01}$ mode probes in the top surface of the enclosure shown in FIGS. 13-15.

FIG. 18 is a schematic view showing measurements of the placement of two $TE_{01}$ mode capacitive coupling probes 162 and 164 in the ceiling 160 of the frame 167 shown in FIGS. 13-15. In this embodiment, the frequency of operation with the RFID tags is 915 MHz, which therefore has a wavelength of 0.32764 meters or 1.07494 feet. One-half wavelength is therefore 0.16382 meters or 6.4495 inches. The length of the capacitive coupling bent portion 200 of each of the probes is 5.08 cm or 2.00 in. The length of the axial extension 202 of the probes into the enclosure is 3.81 cm or 1.50 in., as measured from the insulator 204 into the enclosure 166. The probe configuration and placement in the embodiment was based on an operation frequency of 915 MHz. In one embodiment, the enclosure 166 had a depth of 16.1 inches (40.89 cm), a width of 19.2 inches (48.77 cm) and a height of 3 inches (7.62 cm). It was found that the optimum probe placements for this size and shape (rectangular) enclosure and for the 915 MHz operating frequency were: the front probe was spaced from the front wall by 5.0 inches (12.7 cm) and the rear probe was spaced from the back wall by 5.0 inches (12.7 cm). As discuss above, the probes in this embodiment would only be activated sequentially.

Figure 19:
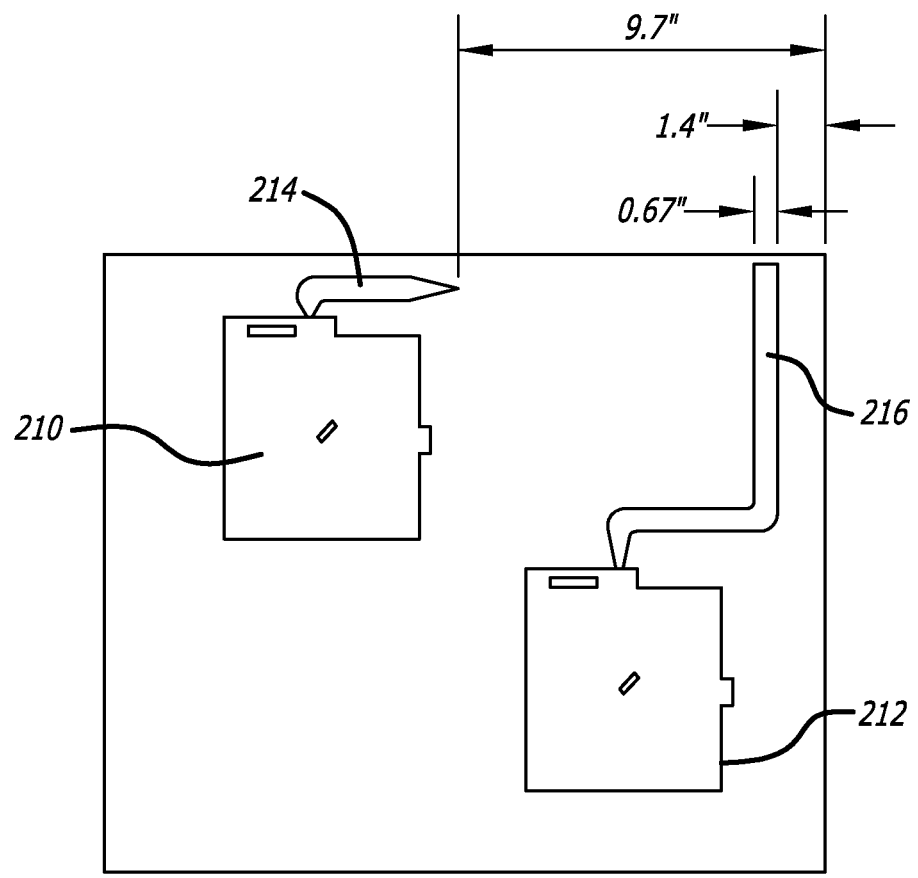
FIG. 19 is a schematic view of the size and placement within the drawer of FIG. 16 of two microstrip or "patch" antennae and their microstrip conductors disposed between respective antennae and the back of the drawer at which they will be connected to SMA connectors in one embodiment, for interconnection with other components.

FIG. 19 is a schematic view of the size and placement within the enclosure 166 of FIG. 16 of two microstrip or "patch" antennae 210 and 212 and their microstrip conductors 214 and 216 disposed between the respective antennae and the back of the enclosure at which they will be connected to SMA connectors (not shown) in one embodiment. Feed lines 58 (FIG. 3) may be connected to those SMA connectors and routed to the computer 44 for use in communicating the RFID signals for further processing. The measurements of the spacing of some of the microstrip components are provided in inches. The spacing of 9.7 in. is equivalent to 24.64 cm. The width of the microstrip line of 0.67 in. is equivalent to 17.0 mm. The spacing of 1.4 in. is equivalent to 3.56 cm. Other configurations and types of receiving antennae may be used, as well as different numbers of such antennae. In the present embodiment, the receiving antennae are mounted on insulation at the bottom inside surface of the metallic enclosure frame 167 so that the receiving patch antennae are not in contact with the metal surfaces of the Faraday cage.

Figure 20:
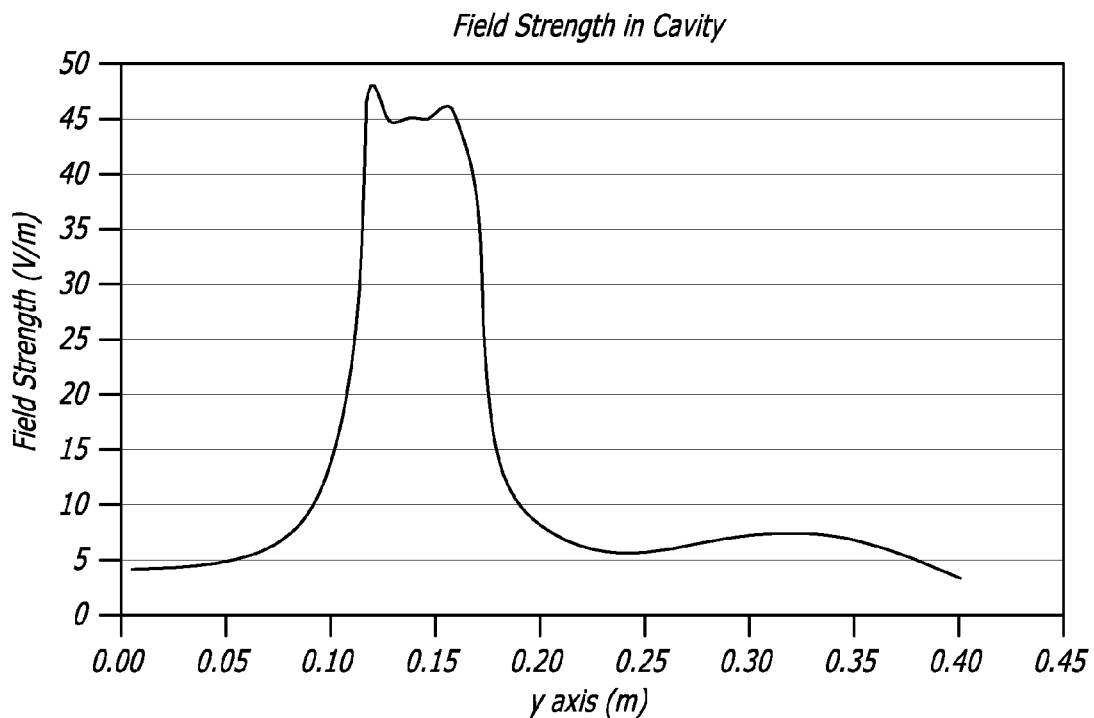
FIG. 20 is diagram of field strength in an embodiment of an enclosure with a probe placed in the enclosure at a position in accordance with the diagram of FIG. 19.
Figure 21:
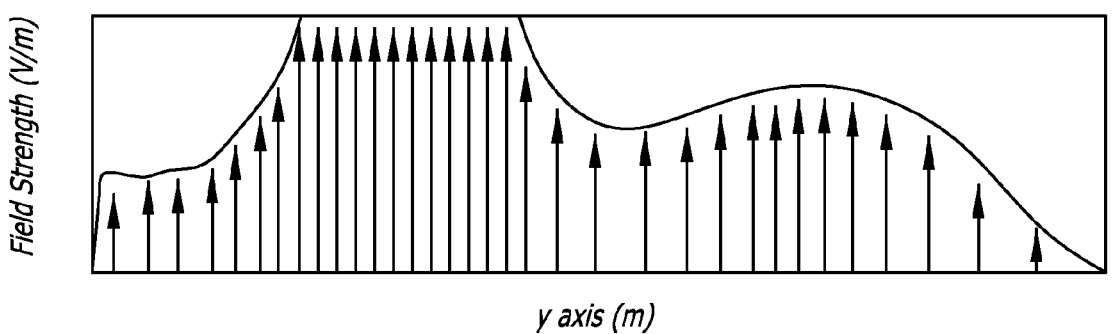
FIG. 21 is a lower scale drawing of the field intensity diagram of FIG. 20 showing a clearer view of the field intensity nearer the front and back walls of the enclosure.

Referring now to FIG. 20, the field intensity or field strength in the enclosure discussed above is shown with the ordinate axis shown in volts/meter and the abscissa axis shown in meters. It will be seen from the diagram that the maximum field intensity occurs at about 5.0 inches (0.127 m) which results from the probe positioned at 5.0 inches (12.7 cm) from the front wall and at a 915 MHz operating frequency. Referring now to FIG. 21, the scale has been reduced although the large rise in field intensity can be seen at 5.0 inches. It can also be more clearly seen that the field intensity falls off at the right wall but remains strong very close to the left wall. Therefore in an embodiment, a second probe was used that was placed 5.0 inches (12.7 cm) from the right wall thereby resulting in a mirror image field intensity to that shown in FIG. 21. The two probes 162 and 164 are activated sequentially and are not both activated simultaneously. It will be noted that better EM field coverage of the enclosure 166 is obtained with the two probes and that RFID tags on articles positioned close to the front wall 161 will be activated by the front probe 162 and that RFID tags on articles positioned close to the rear wall 170 will be activated by the rear probe 164 (see FIG. 13).

Although not intending to be bound by theory, in deriving the probe location for TE modes in a square or rectangular non-resonant cavity, the following equation can be useful:

$$N = 2 \times \frac{L_2 - L_1}{\lambda_g}$$

where: N=positive non-zero integer, for example 1, 2, 3, etc.

L$_1$=distance between probe and back wall
L$_2$=distance between probe and front wall
$\lambda_g$=wavelength in the cavity L$_1$ cannot be zero for TE modes, which implies that the probe for TE mode excitation cannot be at the front or back wall. For TM modes, the equation is the same, but N can equal zero as well as other positive integers. The probe position cannot be $\lambda_g/2$ from the front or back wall. An L$_1$ and an L$_2$ are chosen such that N can be a positive integer that satisfies the equation. For example, for the enclosure 166 discussed above:

L$_1$=4.785 inches
L$_2$=11.225 inches
$\lambda_g$=12.83 inches
Therefore, $$N = 2 \times \frac{11.215 - 4.785}{12.83} = 1.0$$

The actual enclosure had the probe located at a slightly different location (5.0 inches) than that indicated by the equation (4.785 inches) which was possibly due to the insertion of a plastic drawer in the cavity, which introduces a change in the phase from the reflected signals. The equation above is set up such that the reflected phase from both front and back walls is equal, i.e., they are "in phase" at the probe location.

The wavelength in the enclosure, $\lambda_g$, can be calculated using waveguide equations. Equations for a rectangular cavity are shown below. The cutoff frequency is required for this calculation. The equations will change for a cylindrical cavity or for other shapes.

The cutoff frequency is at the point where g vanishes. Therefore, the cutoff frequency in Hertz is:

$$(f_c)_{mn} = \frac{1}{2\pi\sqrt{\mu\varepsilon}} \sqrt{\left(\frac{m\pi}{a}\right)^2 + \left(\frac{n\pi}{b}\right)^2} \text{ (Hz)}$$

The cutoff wavelength in meters is:

$$(\lambda_c)_{mn} = \frac{2}{\sqrt{\left(\frac{m}{a}\right)^2 + \left(\frac{n}{b}\right)^2}} (m)$$

where: a =inside width
b=inside height
m=number of ½-wavelength variations of fields in the "a" direction
n=number of ½-wavelength variations of fields in the "b" direction
$\varepsilon$=permittivity
$\mu$=permeability The mode with the lowest cutoff frequency is called the dominant mode. Since TE$_{10}$ mode is the minimum possible mode that gives nonzero field expressions for rectangular waveguides, it is the dominant mode of a rectangular waveguide with a>b and so the dominant frequency is:

$$(f_c)_{10} = \frac{1}{2a\sqrt{\mu\varepsilon}} \text{(Hz)}$$

The wave impedance is defined as the ratio of the transverse electric and magnetic fields. Therefore, impedance is:

$$Z_{TE} = \frac{E_x}{H_y} = \frac{jw\mu}{j\beta} \Rightarrow Z_{TE} = \frac{k\eta}{\beta}$$

The guide wavelength is defined as the distance between two equal phase planes along the waveguide and it is equal to:

$$\lambda_g = \frac{2\pi}{\beta} > \frac{2\pi}{k} = \lambda$$

$$\text{where } k_c = \sqrt{\left(\frac{m\pi}{a}\right)^2 + \left(\frac{n\pi}{b}\right)^2} \text{ ; and}$$

$$\beta = \sqrt{k^2 - k_c^2}$$

Figures 1, 22:
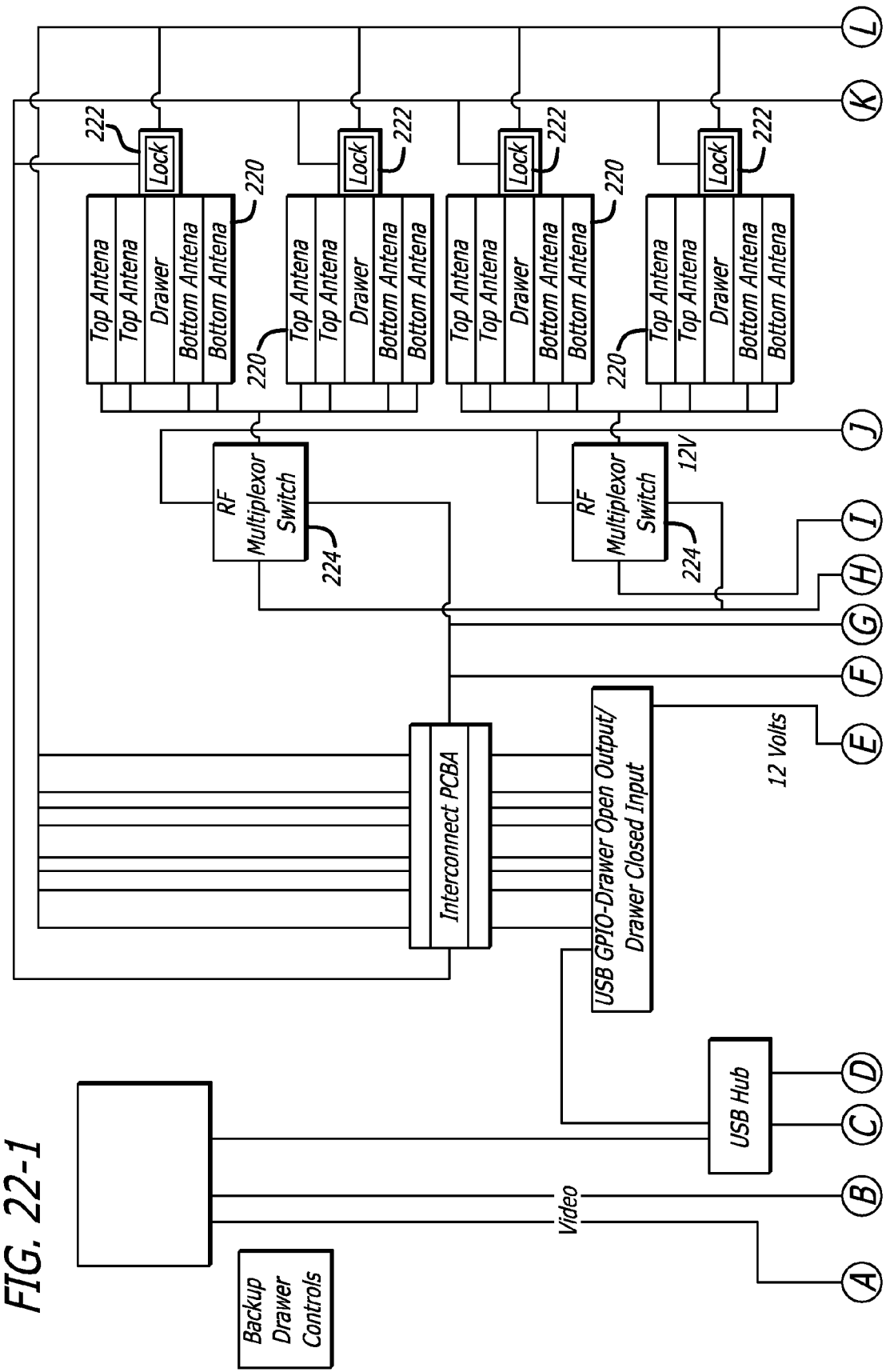
FIG. 22 is a block electrical and signal diagram for a multiple-drawer medical cabinet, such as that shown in FIG. 2, showing the individual multiplexer switches, the single RFID scanner, and power control.
Figures 2, 22:
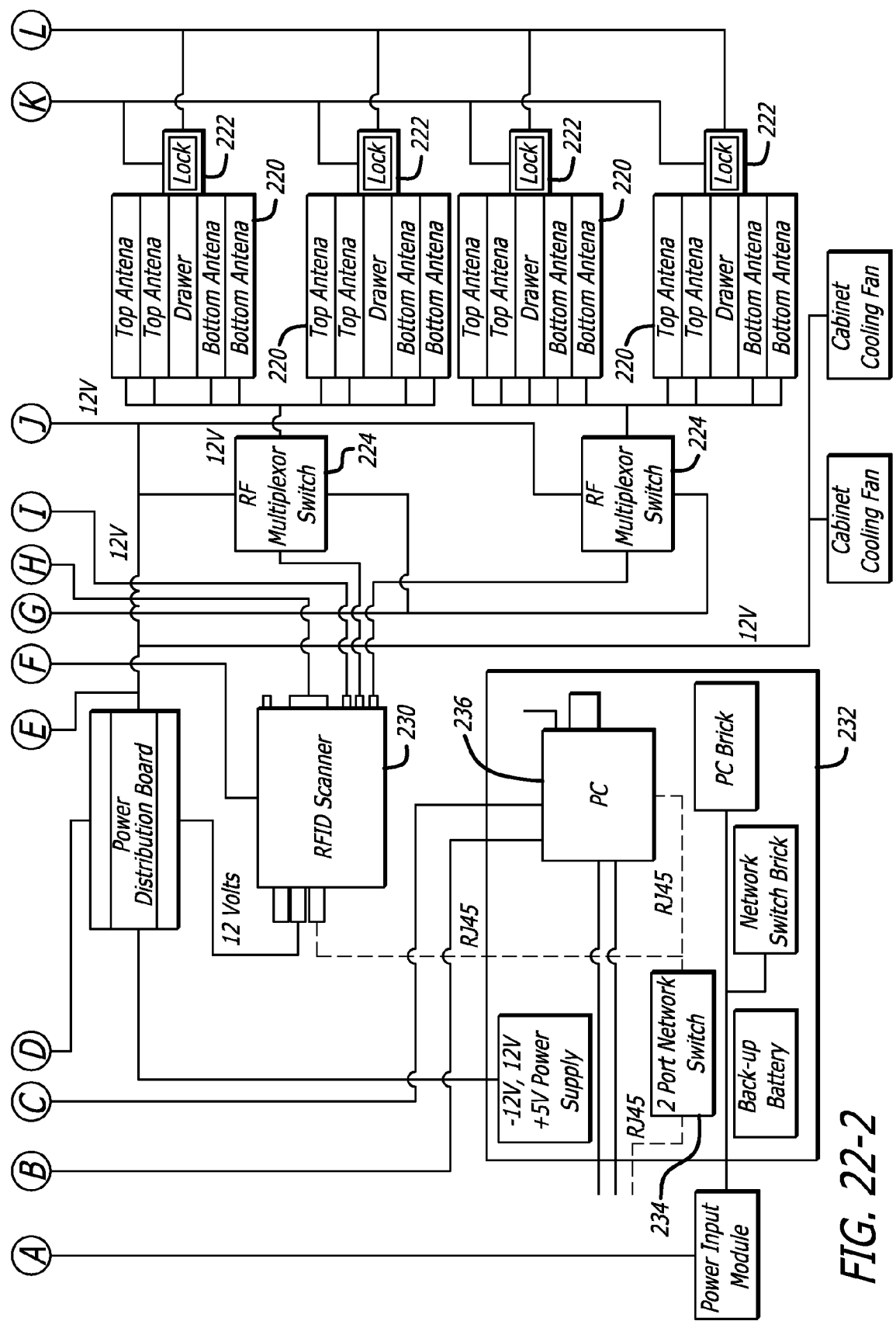
Figure 23:
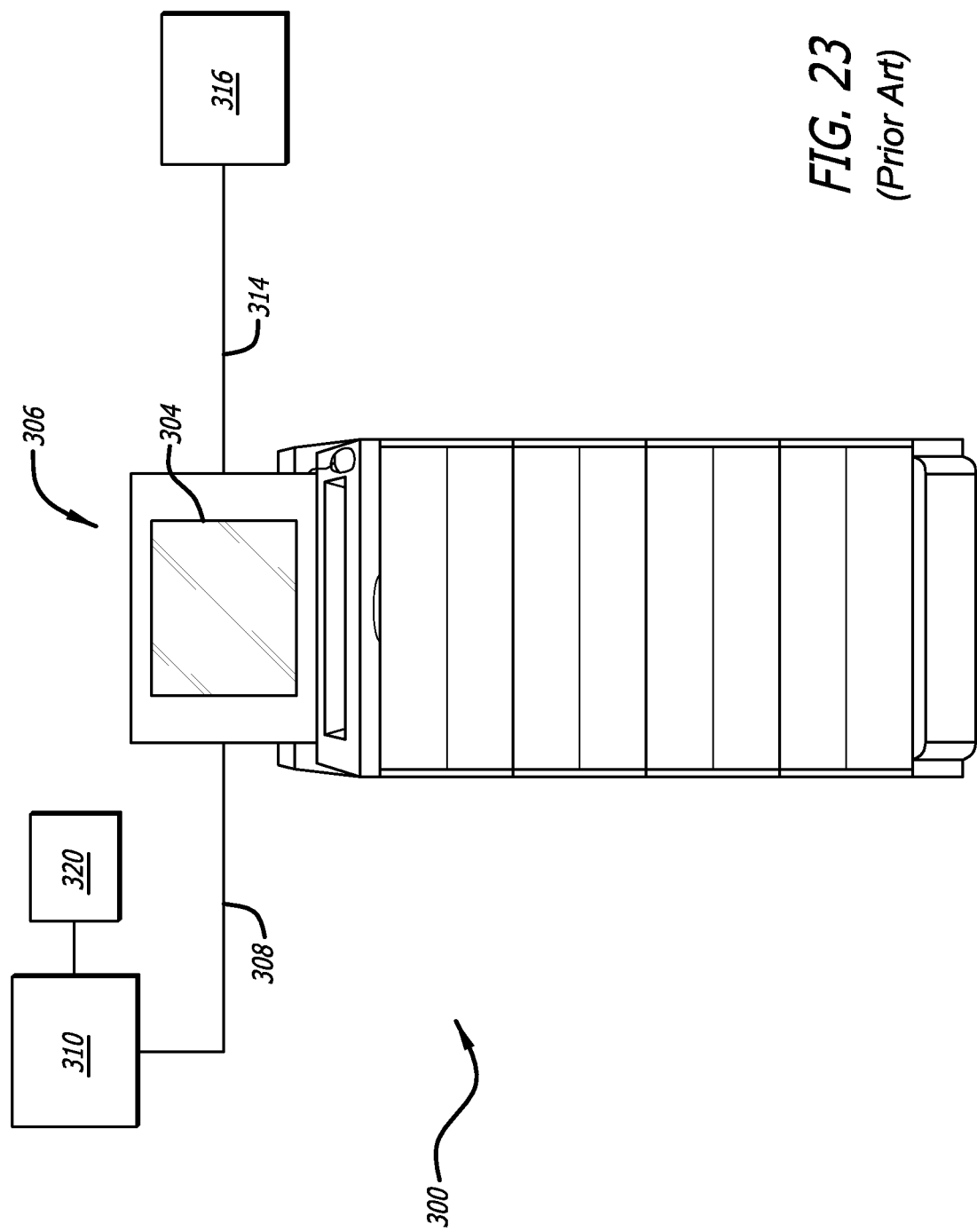
FIG. 23 shows a medication administration cabinet having a control unit, a plurality of drawers and connections to a server and data base.
Figure 24:
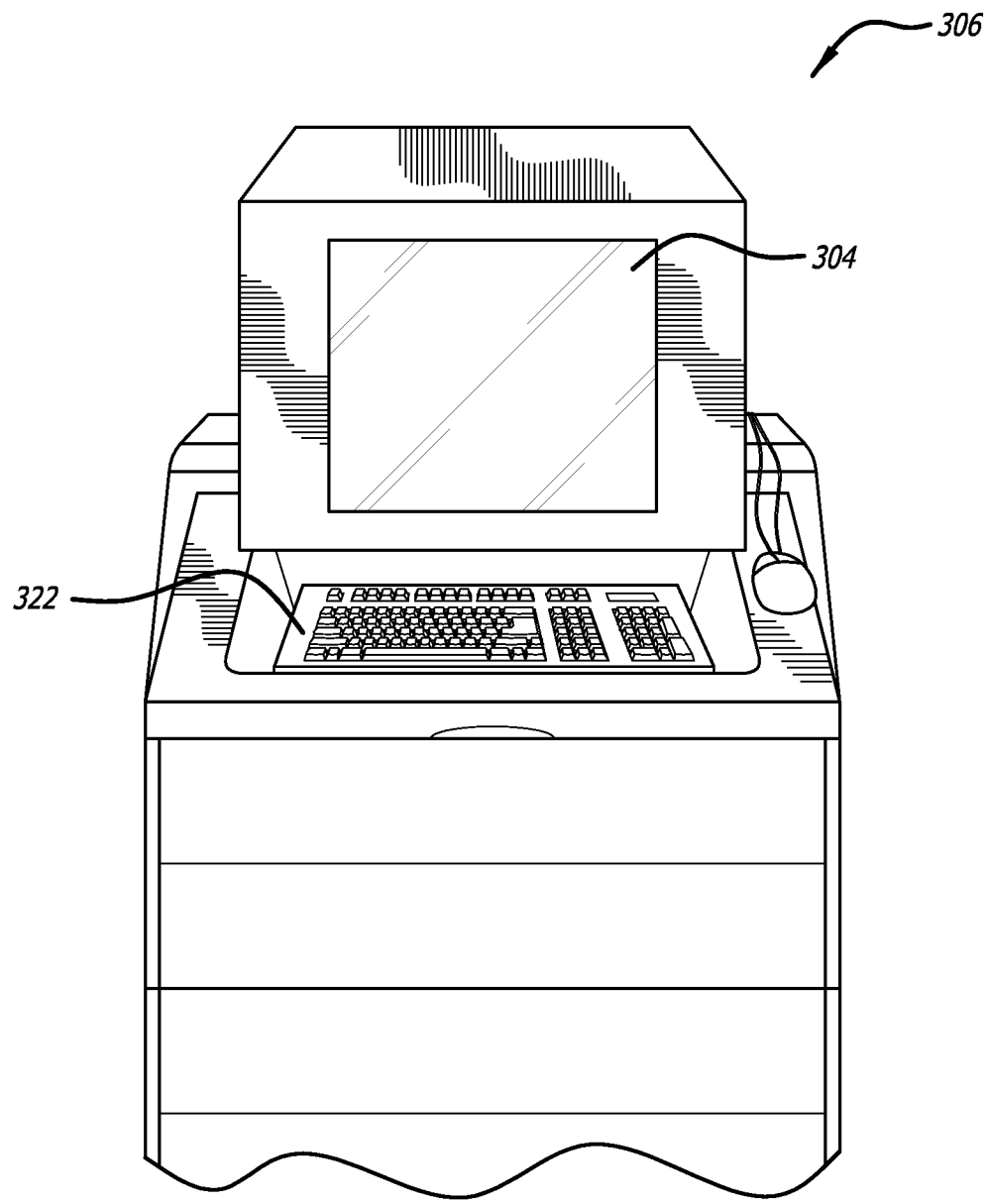
FIG. 24 shows the medication administration cabinet of FIG. 23 with a view of two input devices, one of which is a keyboard and the other of which is a pointing device in the form of a "mouse;"

FIG. 22 provides a block electrical and signal diagram for a multiple-drawer medical cabinet, such as that shown in FIG. 2. In this case, the cabinet has eight drawers 220. Each drawer includes two top antennae, two bottom antennae and a lock with a lock sensor 222 for securing the drawer. Signals to and from the antennae of each drawer are fed through an RF multiplexer switch 224. Each RF multiplexer switch 224 in this embodiment handles the routing of RF signals for two drawers. RFID activation field and RFID received signals are fed through the respective RF multiplexer switch 224 to a main RFID scanner 230. The scanner 230 output is directed to a microprocessor 232 for use in communicating relevant information to remote locations, in this case by wired connection 234 and wireless connection 236. Various support systems are also shown on FIG. 20, such as power connections, power distribution, back up battery, interconnection PCBA, USB support, cooling, and others.

In accordance with one embodiment, drawers are sequentially monitored. Within each drawer, the antennae are sequentially activated by the associated multiplexer 224. Other embodiments for the signal and electrical control systems are possible.

Although RFID tags are used herein as an embodiment, other data carriers that communicate through electromagnetic energy may also be usable.

Refrigerated Drawer

Figure 25:
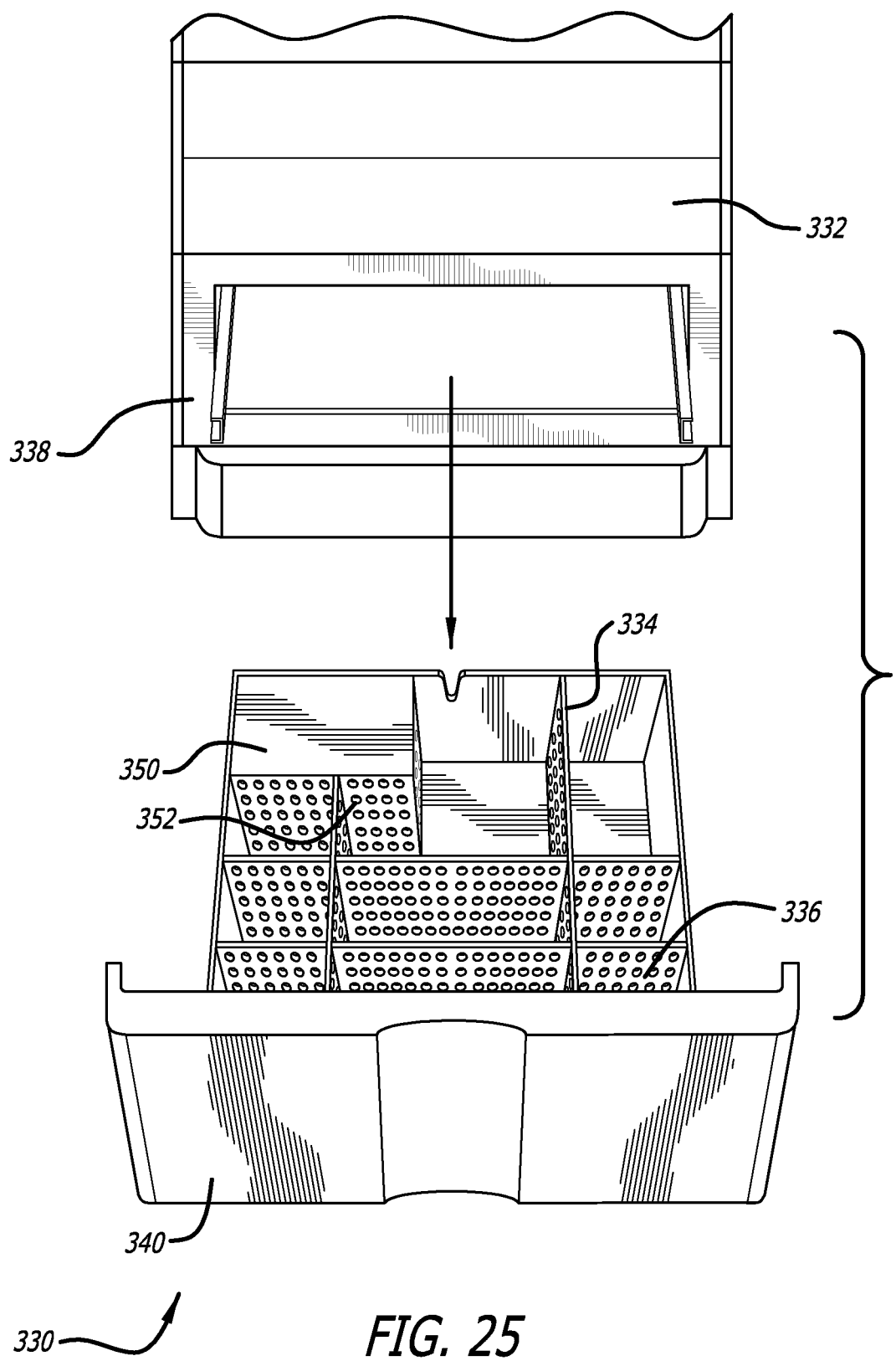
FIG. 25 is an exploded view of a drawer removed from the opening and Faraday cage of the medication cabinet, showing details of the drawer design including partitions for creating pockets to store medical items, a TEC enclosure at the rear of the drawer, and part of the Faraday cage created in the cabinet.
Figure 26:
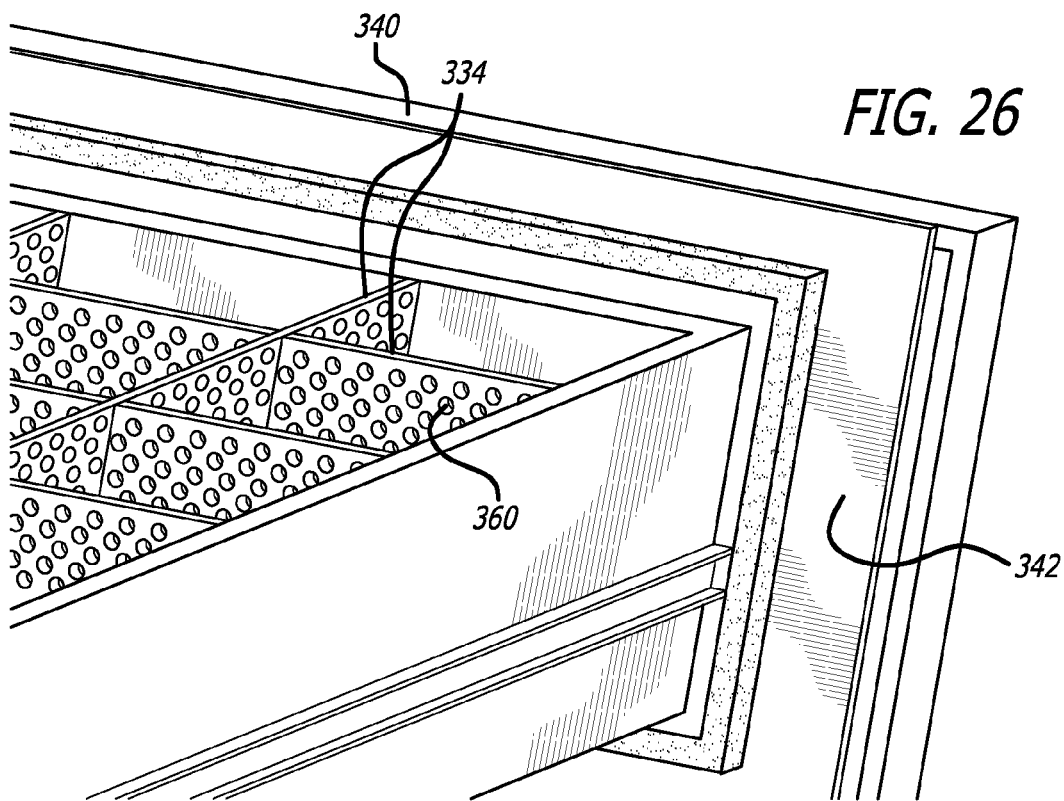
FIG. 26, is an enlarged view of the drawer of FIG. 25 looking from behind the drawer so that the metallic front of the drawer can be seen, which, when the drawer is in the closed position, completes the Faraday cage about the drawer so that the RFID system will operate effectively.

Referring now to FIG. 25, a generally non-metallic slidable drawer 330 is configured to be mounted within a medication cabinet 332. It includes various dividers or partitions 334 in the drawer that form "pockets" 336 within which are placed medical articles for storage and administration. The cabinet within which the drawer is slidably mounted includes a metallic frame 338 surrounding the drawer to operate as a Faraday cage. Also now referring to FIG. 26, the front portion 340 of the drawer 330 may be formed of metal 342 or include a metallic portion that contacts the remainder of the metallic frame 338 of the cabinet 332 when the drawer is in the closed configuration to complete the Faraday cage around the drawer. Within that frame is included an RF system for detecting the existence of RFID tagged articles placed in the drawer as discussed above in further detail.

Figure 30:
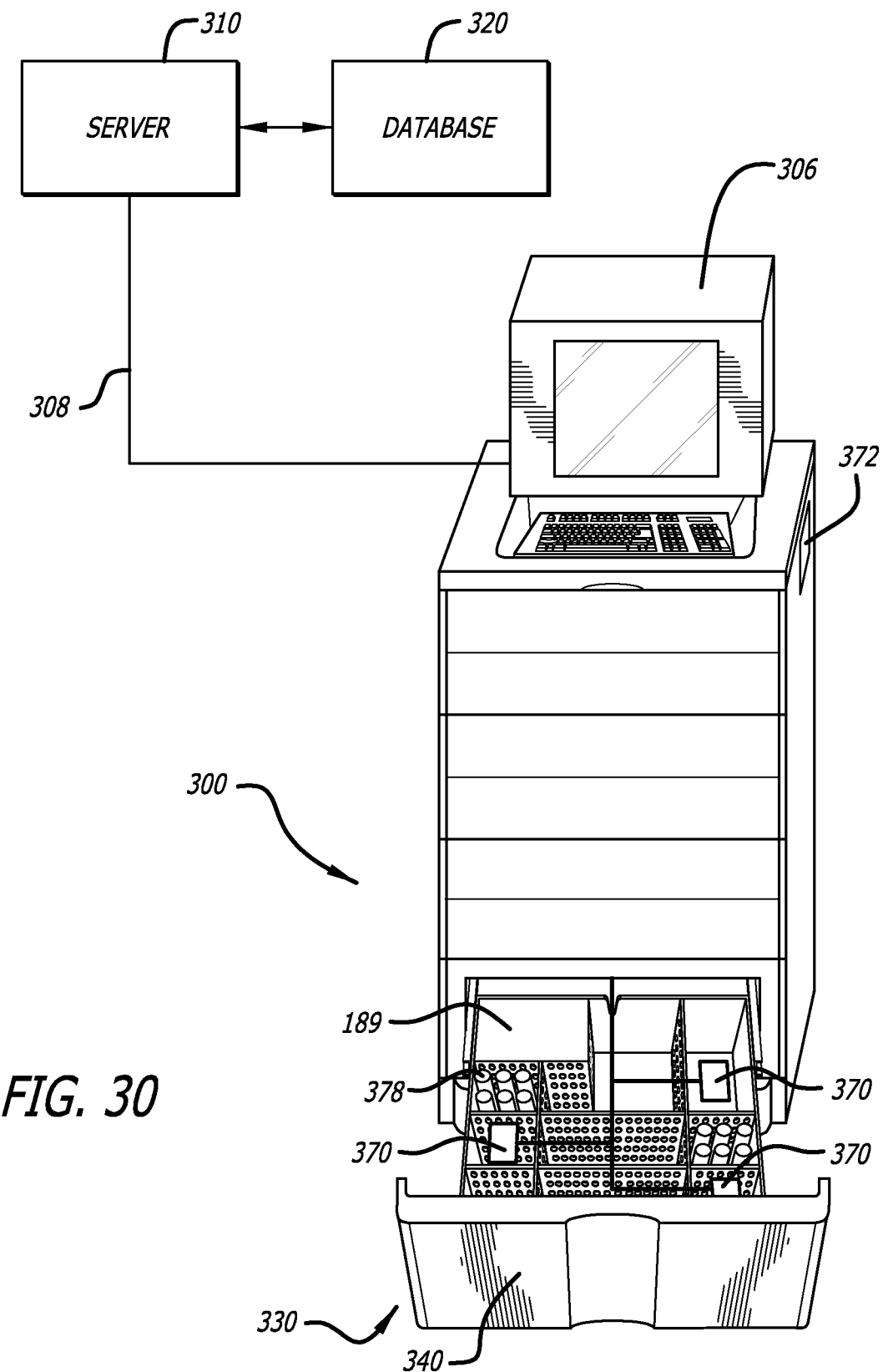
FIG. 30 presents a perspective view of a system in accordance with aspects of the invention showing an open refrigerated drawer with a mounted TEC device, mediations in pockets of the drawer, three temperature sensors in pockets, and ambient temperature sensor, control unit, and connection with a server and data base.

Referring now to FIG. 16, in accordance with another aspect of the invention, a thermoelectric cooling ("TEC") device 189 is disposed at the back of the metallic frame 170. See also FIG. 30 showing the position of a TEC device 189 that has been mounted to the drawer and moves with it to the open and closed positions. In one embodiment the TEC device is located at a corner of the back of the drawer as opposed to being centrally located. An RFID reader 182 for detecting RFID tagged articles in the drawer 180 is included in the frame about the drawer with the probes 162, 164 being centrally placed above the drawer in this embodiment. Therefore, there is less room available for a TEC device 189 in the center of the drawer. Additionally, it was noticed by the inventors that the TEC device must actually extend somewhat into the drawer due to a need to keep the medication cabinets and drawers at a smaller size. When the TEC device is located at a corner of the back of the drawer, it was found that it only interferes with two pockets 336 of the drawer, as seen in FIG. 25. However, if it is placed in the center of the drawer, it would interfere with three pockets, thereby resulting in less storage room for storing medical articles in a drawer.

In an embodiment of the invention, a Peltier TEC device 189 was used. Such units are available from TE Technology, Inc., having an address of 1590 Keane, Traverse City, Mich., part number AC-073 (www.tetech.com). In this embodiment, a Peltier-type unit was used due its small size, semi-conductor nature, availability, and sufficient cooling capacity. The use of such units provides significant advantages, one of which is the lack of vibration since no compressor is needed. However, the invention is not limited to only thermo-cooling type units, but others that exist now or may become available in the future can be used.

One of the advantages of the invention is that a cabinet of the present embodiment has both cooled and uncooled drawers. In the prior art, cabinets were either completely refrigerated or completely non-refrigerated as was discussed in detail above in the Background section. This is an undesirable approach since two cabinets are necessary for the two different types of medications, one of which requires constant cooling, and the other of which needs to be at room temperature for use. Thus, a cabinet that is able to provide both refrigerated and non-refrigerated drawers is needed in the art and is provided here.

Figure 27:
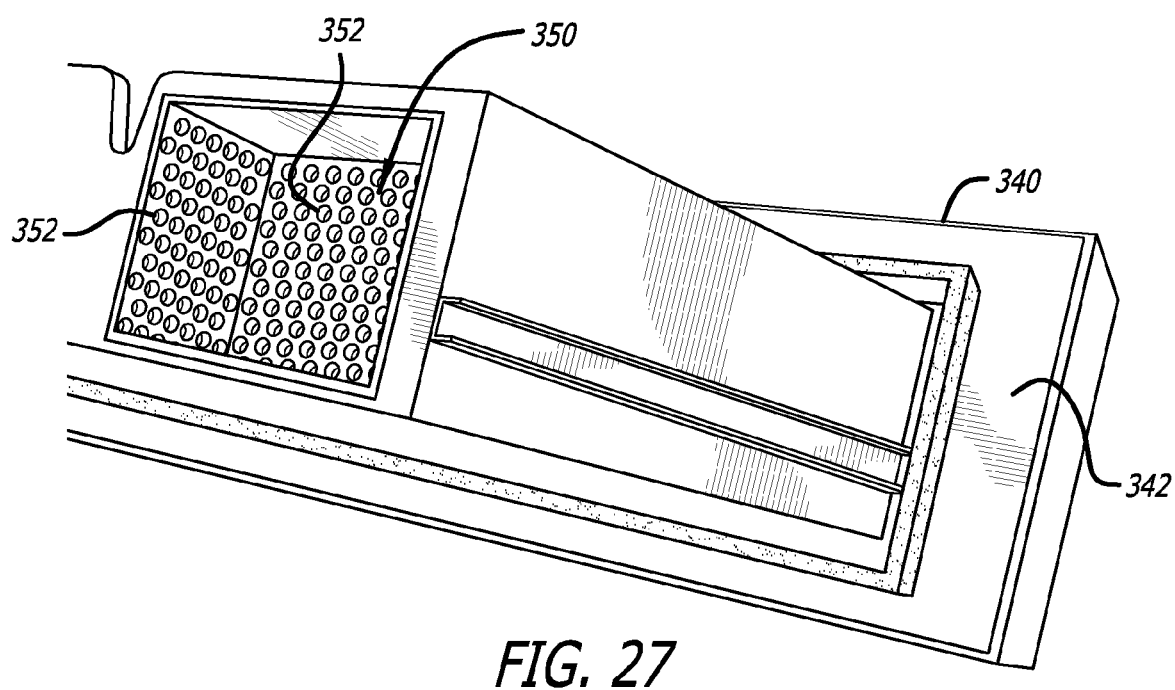
FIG. 27 is another view of the drawer of FIG. 25 showing the TEC device enclosure in greater detail at the back of the drawer, showing the thermal diffuser formed into the enclosure.

Referring again to FIG. 25 and also to FIG. 27, a TEC device enclosure 350 is shown at the rear corner of the drawer 330. In FIG. 25, this enclosure 350 is covered but FIG. 27 shows it more clearly. This enclosure is a part of the "real estate" of the drawer and is used to receive the TEC device when the drawer is in the closed position. It will be noted that holes 352 are formed in the enclosure 350 in the front and side partitions 334 which operate to diffuse the cooling effect of the TEC device. FIG. 16 also shows that the TEC device 189 of this embodiment includes a fan 188 that, when combined with the diffuser, lowers or eliminates any temperature gradients that may tend to exist in the drawer 330 (FIG. 25). The size and locations of the partitions 334 also assist in lowering any temperature gradients as well as the holes 360 formed in the partitions.

In one embodiment, the TEC device 189 is anchored to the frame of the cabinet 300 and the drawer 330 engages it when closed and is moved away from it when open. This configuration is shown in FIG. 16. This permits ambient air to have a greater effect on the contents of the drawer when the drawer is in the open position. In another embodiment as shown in FIG. 30, the TEC device is anchored to the drawer 330 and moves with the drawer when the drawer is opened. This will permit the cooler air from the TEC device to be continually present thus lessening the effect of the ambient air on the drawer contents when the drawer is open.

Figure 28:
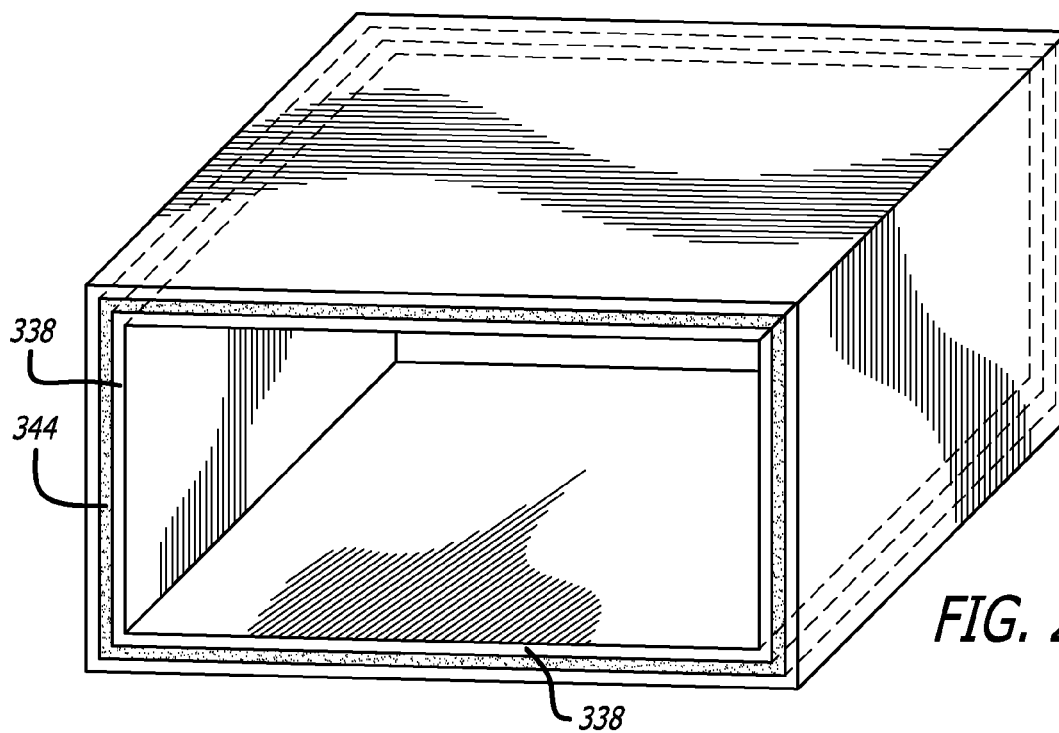
FIG. 28 is a more detailed view of the construction of the part of the cabinet surrounding a refrigerated drawer showing slabs of insulation around the top, bottom, and sides of the drawer, and the metallic liner for forming the Faraday cage.
Figure 29:
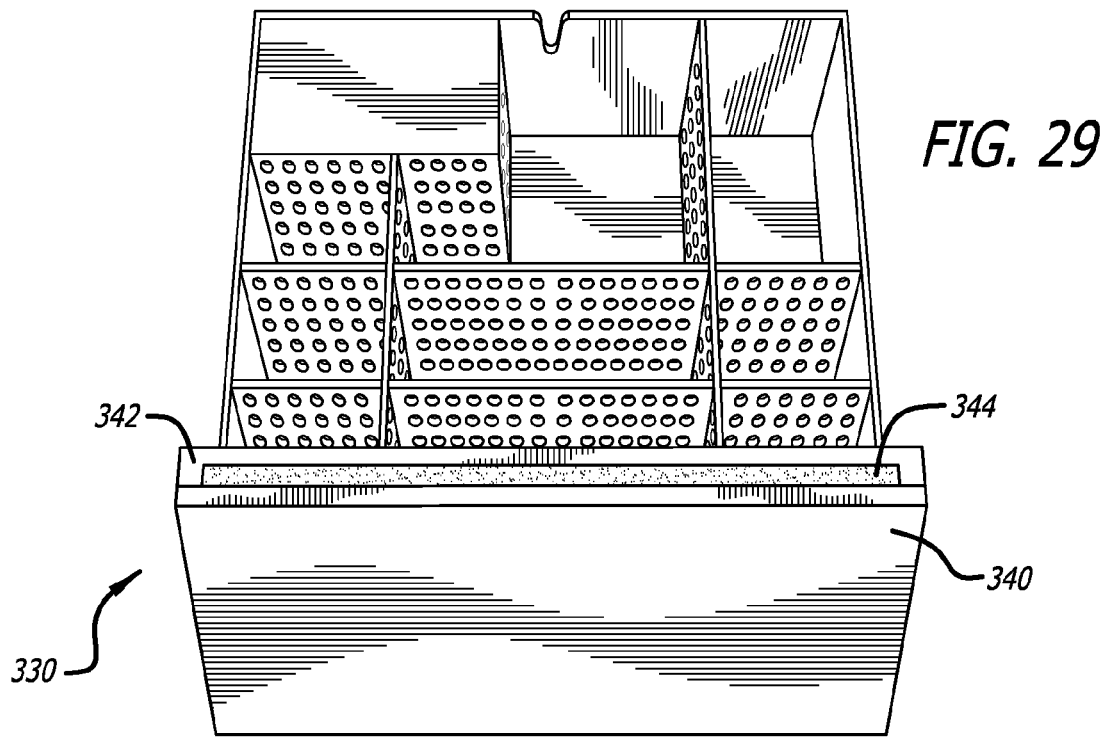
FIG. 29 presets a partial view of the front of the drawer showing the insertion of insulation in the front panel of the drawer.

Returning again to the drawer 330, an RF drawer as contemplated by the invention uses both electrical insulation and thermal insulation. The electrical insulation is provided by locating electrically conductive materials about the drawer on all sides to form the required Faraday cage, some of which is shown in FIG. 25 as the frame 338 and as shown in FIG. 28, which shows a portion of the cabinet with a drawer removed. The thermal insulation 344 is provided by the use of standard thermal insulation available widely. In some cases where large surface areas are available, slabs of the thermal insulation are cut at the appropriate sizes and installed in the framework around the location of the drawer 330 as shown in FIG. 28. As shown in FIG. 29, the front 340 of the drawer 330 may also have insulation 344 located within it. In areas such as the back of the drawer where there are electrical conductors and other equipment used in conjunction with the drawer, spray-type insulation (not shown) may be used after the manufacture of the drawer is completed to place the required thermal insulation around the drawer. Use of a high quality thermal insulation, such as Semi-Rigid PVC Foam, not only keeps the cool air within the drawer when the drawer is in the closed position, but also protects adjacent drawers from cooling produced by the TEC device 189 for that particular drawer. It has been found that with the proper amount of insulation, adjacent drawers are at room temperature while the refrigerated drawer may be held at a range of 3-10° C.

In one embodiment, the TE Technology Peltier thermoelectric cooler module 189 listed above was used and had a capacity of 73 watts at a 0° temperature difference. The medication cabinet 300 in which it was installed for refrigerating a single drawer 330, held a total of 5 drawers. It was found that by using a Peltier unit of this capacity with the surrounding insulation approach discussed above and shown in the drawings, the target drawer was kept at the temperature desired and adjacent drawers were able to remain at room temperature. Furthermore, the power requirements and size of the TEC device are substantially reduced compared to the traditional compressor-based systems.

In another feature, the TEC devices 189 for the drawers 330 of the cabinet 300 may be selectively turned off so that the cooling system is not running and the drawer can be at ambient temperature. This allows the healthcare facility to lower costs since the TEC device 189 will not needlessly be consuming electricity.

In a further feature, the drawers 330 include at least one temperature sensor 370. The temperature data from these sensors are communicated to the control unit 306 for monitoring. Should the temperature of a refrigerated drawer rise above a selected threshold, an alarm may be provided at the display 304. Additionally the control unit 306, server 310, and data base 320 may cooperate to conduct temperature data logging for historical charting and analysis. In the embodiment of FIG. 30, an ambient temperature sensor 372 is provided. This sensor is located at a position away from the heat exhaust of the TEC device or devices so that its reading is not influenced by those exhausts. Having a single ambient temperature sensor obviates the need for a sensor in each of the non-refrigerated drawers. Since those drawers have no temperature control devices affecting them, it is presumed that they are at the ambient temperature.

This invention utilizes a data base 320 that a healthcare institution can maintain to list medications and other medical supplies that require refrigerated conditions. In addition, there is an RFID system that determines the need for and controls the environment of refrigerated medications within an RFID-enabled dispensing cabinet 300 or mobile cart 318. The system will automatically determine via the database what conditions a medication that has been loaded into it will require and make the necessary inputs/outputs to insure the medication's environmental requirements are maintained as well as recorded on a pre-determined time interval basis for history record purposes.

When a medication 378 is placed into the RFID dispensing cabinet 300 or mobile cart 316, the system recognizes the need for refrigeration, if required. This recognition may occur in different ways. In one way, the RFID tag associated with the medication may be coded to indicate that temperature control is required and at what temperature. In another way, the control unit 306 receives the identification of the medication in the drawer 330 from the RFID detection system, accesses the remote server 310 and its data base 320, and receives the data about this identified medication indicating that the medication needs temperature control and the temperature required.

Figure 31:
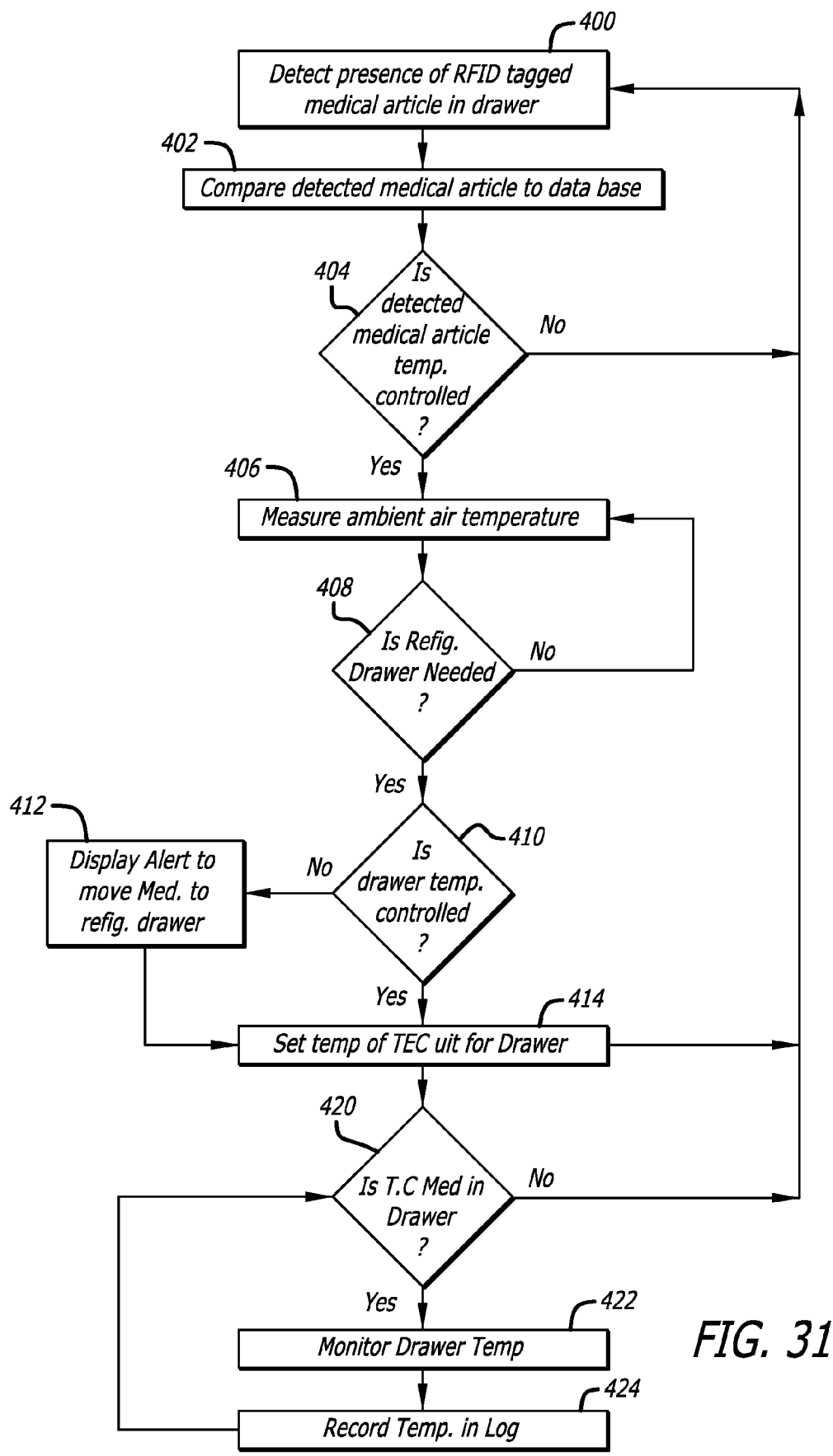
FIG. 31 presents a method in accordance with aspects of the invention providing an automatic system for detecting temperature controlled medications, determining the temperature requirements for those medications, and controlling the TEC device to maintain the required temperature, with the figure also showing a temperature data logging system to satisfy requirements imposed by healthcare authorities.

A "smart" system via the host computer 306 determines the need for refrigeration and effects the necessary outputs to provide the correct environmental conditions for such. Turning in more detail to FIG. 30 and to FIG. 31, a system and method are presented for this "smart" system. In FIG. 30, a cabinet 300 is shown with a drawer 330 open. Pockets of the drawer are shown and some of those pockets contain medications 378, each of which has an RFID tag. When the drawer is pushed back into the cabinet, the RFID system automatically detects the tag of the medication and reads it 400. In one embodiment, the control unit 306 receives the data from that RFID tag, automatically contacts the remote server 310 and looks up 402 the medication in the data base 320. The control unit then determines if the medication requires temperature control 404. If it does require temperature control, the control unit automatically measures the temperature of the ambient air 406 through reference to the ambient air sensor 372 to determine if a refrigerated drawer is needed 408. If the ambient air temperature meets the requirement for the temperature controlled medication 378, the control unit then continues to monitor the ambient temperature to be sure that no changes are occurring.

In another embodiment, the RFID tag placed on each medication 378 includes a temperature sensor, and part of the data transmitted by the RFID tag for that medication includes the temperature of the medication.

If the ambient temperature is not consistent with the temperature requirement of the medication, the control unit determines if the drawer in which the medication has been placed can be temperature controlled 410. If it cannot, an alert is automatically provided 412 that the medication must be moved to a refrigerated drawer. Once the medication is moved to a refrigerated drawer, the RFID system once again automatically determines its presence in that drawer and the control unit 306 then sets the temperature 414 for the TEC device to maintain for the medication.

Another feature in accordance with aspects of the invention is that temperature monitoring and logging occur. The control unit 306 determines if a temperature controlled (TC) medication is located in a drawer 420. If so, the temperatures sensors 370 of that drawer are monitored 422 by the control unit 306 and are periodically logged 424 as required by the policies of the healthcare institution or other authorities. When needed, the logs may be printed or forwarded elsewhere in digital form.

Figure 32:
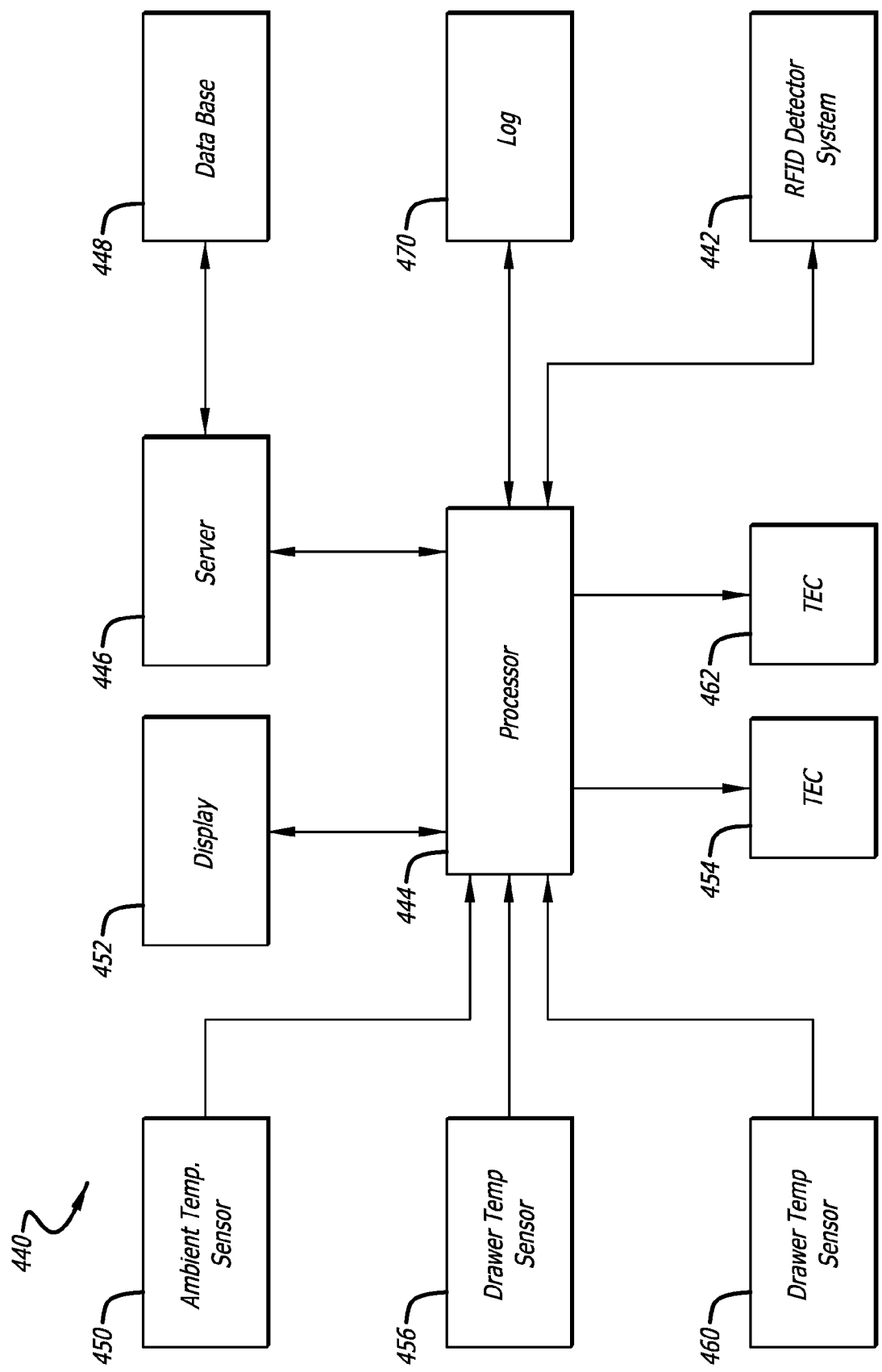
FIG. 32 is a block diagram of a system in accordance with aspects of the invention in which an RFID detector system detects the presence of temperature controlled medical items, notifies a processor which identifies the temperature requirement for the detected medication, and controls the TEC device in a drawer to maintain the required temperature, the processor also programmed to create a log of temperature events while the medication is in the cabinet.

Turning now to FIG. 32, a block diagram of a system 440 in accordance with aspects of the invention is shown. An RFID detector system 442 located in a drawer of a cabinet detects the existence of a medical item having and RFID tag. The detector system 442 provides the data read from the RFID tag to the processor 444. The processor then accesses the server 446 and the associated data base 448 to determine the characteristics of the detected medical item and to determine if it has any temperature control requirements. Other data about the medical item may be of importance in tracking the item, and for other purposes.

If the medical item requires temperature control, the processor accesses the ambient temperature sensor 450 to determine if the ambient temperature satisfies the medical item's requirements. If the medical item needs a temperature below the ambient temperature, the processor will determine if the medical item is currently in a temperature controlled drawer of the medical cabinet. If it is not, the processor will display an ALERT message on the display 452 to have a user move the medical item to a temperature controlled drawer. Once this has been done, the RFID detector system 442 will automatically detect the presence of the medical item in a temperature controlled drawer and will inform the processor 444. The processor will then set the TEC device 454 of that drawer to the correct temperature to be maintained. The TEC device will automatically maintain the temperature of that drawer to the temperature required for the medical item. The system 440 of FIG. 32 may have another one or more temperature controlled drawers with a sensor 460 and TEC device 462.

The same is true of removal of the temperature controlled medication from a drawer. The processor monitors all medications delivered to the drawer and removed from the drawer and automatically controls the refrigeration device accordingly. If there are no more medications left in the drawer that have temperature control requirements, the processor will automatically deactivate the refrigeration unit of that drawer and allow the drawer to return to ambient temperature, thus conserving energy.

In another feature, the processor monitors the temperature sensor 456 of that drawer and creates a log 470 concerning that medical item and the sensed temperature at which it was kept, at intervals as required, for example twice per day. The log may be kept in a processor memory, forwarded to a server, or otherwise stored or printed. Various details may be included in the log, such as cabinet identification, drawer identification, temperature sensor type, calibration date, arrival date and time, removal date and time, and other data, as required.

Thus an RFID enabled drawer refrigeration system provides numerous advantages. Selective cooling of certain drawers may occur while other drawers are at room temperature. Because of this feature, only one cabinet is needed for both refrigerated medical articles and room temperature medical articles. There is a modular design in that the drawers are configuarable and selectable between refrigerated and ambient temperatures.

Unless the context requires otherwise, throughout the specification and claims that follow, the word "comprise" and variations thereof, such as, "comprises" and "comprising" are to be construed in an open, inclusive sense, which is as "including, but not limited to."

While the invention has been described in connection with what is presently considered to be the most practical and preferred embodiments, it is to be understood that the invention is not to be limited to the disclosed embodiments and elements, but, to the contrary, is intended to cover various modifications, combinations of features, equivalent arrangements, and equivalent elements included within the spirit and scope of the appended claims.

We claim:

1. A cabinet for storing medical items, the cabinet having a depth and comprising:
   a plurality of drawer cavities, each cavity configured to receive a drawer, each cavity having a front opening through which the drawer is moved to a closed position within the cavity and through which each drawer is moved to an open position in which the drawer is at least partially outside of the cavity;
   an electrically conductive cage formed about a first cavity, the cage having a cage front located at the front opening of the cavity;
   a plurality of drawers, each of which is received by a respective cavity and which is movable to an open position and to a closed position, with a first drawer being received by the first cavity having the electrically conductive cage;
   a thermo-electric cooling ("TEC") device configured to provide cooling for a single drawer, the TEC device mounted to at least one of: the first drawer so as to move with the drawer; and at a fixed position in relation to the first cavity;
   a second cavity adjacent the first cavity, the second cavity having no TEC device and being at ambient temperature;
   thermal insulation disposed between the first and second cavities, the thermal insulation located and configured to inhibit cooling provided by the TEC device of the first cavity from reaching a drawer that is located in the second cavity; and
   an RFID reader disposed within the first cavity and configured to read RFID tag data from an RFID tag located within the first drawer.

2. The cabinet of claim 1 wherein the TEC device is mounted in a fixed position in relation to the first cavity such that the first drawer moves toward the TEC device when the drawer is moved to the closed position and moves away from the TEC device when the drawer is moved to the open position.

3. The cabinet of claim 2 wherein the first drawer includes a TEC device enclosure formed at a rear portion of the first drawer, the TEC device enclosure being configured to receive the TEC device into the TEC device enclosure when the drawer is in the closed position, whereby the depth of the cabinet is reduced.

4. The cabinet of claim 3 wherein the TEC cooling device enclosure comprises a diffuser located and configured to assist in diffusing and circulating cooling from the TEC device more equally throughout the first drawer.

5. The cabinet of claim 4 wherein the first drawer having the TEC device enclosure further includes partitions disposed in the first drawer to separate items from one another when stored in the first drawer, the partitions having openings configured such that cooling from the TEC device is allowed to circulate throughout the first drawer through the openings of the partitions.

6. The cabinet of claim 1 wherein the first drawer is slidable into and out of the first cavity, the drawer having a front panel that is electrically conductive and that contacts the front of the electrically conductive cage when the drawer is slid to the closed position thereby completely closing the electrically conductive cage about the first drawer.

7. The cabinet of claim 1 further comprising:
   a temperature sensor located so as to measure temperature in the first drawer and to provide temperature data representative of the sensed temperature,
   a control unit programmed to receive the sensed temperature data, compare it to a selected temperature, and control the TEC device to maintain temperature in the first drawer at a selected level.

8. The cabinet of claim 7 wherein the control unit is further programmed to record the received temperature data from the first drawer sensor in a memory.

9. The cabinet of claim 1 further comprising:
   a temperature sensor located to measure temperature in the first drawer and to provide temperature data representative of the sensed temperature;
   a control unit programmed to receive RFID tag data from the RFID reader regarding an item located in the first drawer and receive sensed temperature data from the temperature sensor regarding the temperature of the first drawer;
   wherein the control unit is further programmed to:
   determine from the received RFID tag data whether an item residing in the first drawer requires a particular temperature;
   if the control unit determines that an item residing in the first drawer does require a particular temperature, then compare that temperature to the sensed temperature data; and
   control the TEC device to maintain the particular temperature in the first drawer.

10. The cabinet of claim 9 wherein the control unit is further programmed to receive RFID tag data having temperature requirements included said RFID tag data and control the TEC device in accordance therewith.

11. The cabinet of claim 9 wherein the control unit is further programmed to:
    receive from the RFID reader RFID tag data that comprises an identification of the RFID tag that was read by the reader;
    access a data base that correlates RFID tag identification data to a particular item and from a correlation of the received RFID identification data, identify an item, and from a data base, determine whether the identified item has a temperature requirement and if so, control the TEC device in accordance therewith.

12. The cabinet of claim 9 wherein the control unit is further programmed to:
    receive RFID tag data that comprises an identification of the tag;
    determine from the received RFID tag data whether any item residing in the first drawer requires a particular temperature;
    if the control unit determines that no item residing in the first drawer requires a particular temperature, then control the TEC device to stop operating.

13. The cabinet of claim 9 further comprising an ambient temperature sensor located to sense ambient temperature around the cabinet and provide ambient temperature data representative thereof;
    wherein if the control unit determines from RFID tag data that an item residing in the first drawer requires a particular temperature, the control unite is further programmed to compare the sensed ambient temperature data to that required temperature and if the ambient temperature satisfies the required temperature, allow the TEC device to remain off.

14. The cabinet of claim 9 wherein the control unit is further programmed to determine if a plurality of items residing in the first drawer require particular temperatures, and if so, then compare those required temperatures to one another, and if the compared required temperatures differ, provide an alert that non-compatible temperature-control items reside in the same drawer.

15. The cabinet of claim 1 further comprising:
a second RFID reader disposed within the second cavity and configured to read RFID tag data from an RFID tag located within the second drawer;
a control unit programmed to receive RFID tag data from the second RFID reader regarding an item located in a non-temperature controlled second drawer;
the control unit further programmed to determine from the received RFID tag data whether an item residing in the second drawer requires a particular temperature, and if the control unit determines that an item residing in the second drawer does require a particular temperature, then provide an alert that a temperature-controlled item has been placed in the second drawer.

16. The cabinet of claim 15 further comprising an ambient temperature sensor located to sense ambient temperature around the cabinet and provide ambient temperature data representative thereof;
wherein the control unit is further programmed to determine from RFID tag data that an item residing in the second drawer requires a particular temperature, comparing the sensed ambient temperature data to that required temperature, and if the ambient temperature satisfies the required temperature of the item in the second drawer, provide an alert that a temperature-controlled item has been placed in the second drawer but that ambient temperature presently satisfies the temperature requirement of said item.

17. A cabinet for storing medical items, comprising:
a plurality of drawer cavities, each cavity configured to receive a drawer, each cavity having a front opening through which the drawer is moved to a closed position within the cavity and through which each drawer is moved to an open position in which the drawer is at least partially outside of the cavity;
a plurality of drawers, each of which is received by a respective cavity and which is movable to an open position and to a closed position;
a thermo-electric cooling ("TEC") device configured to provide cooling for a single drawer, the TEC device mounted at a fixed position in relation to the first cavity;
wherein a second cavity located adjacent the first cavity has no TEC device and is at ambient temperature;
thermal insulation disposed between the first and second cavities, the thermal insulation located and configured to inhibit cooling provided by the TEC device of the first cavity from reaching a drawer that is located in the second cavity;
a first RFID reader disposed within the first cavity and configured to read RFID tag data from an RFID tag located within the first drawer;
a second RFID reader disposed within the second cavity and configured to read RFID tag data from an RFID tag located within the second drawer;
a temperature sensor located to measure the temperature in the first drawer and to provide temperature data representative of the sensed first drawer temperature;
a control unit programmed to receive RFID tag data from the first RFID reader regarding an item located in the first drawer and receive sensed temperature data from the first drawer temperature sensor regarding the temperature of the first drawer;
wherein the control unit is further programmed to:
determine from the received RFID tag data whether an item residing in the first drawer requires a particular temperature;
if the control unit determines that an item residing in the first drawer does require a particular temperature, then compare that temperature to the sensed temperature data;
control the TEC device to maintain the particular temperature in the first drawer; and
record the received temperature data from the first drawer sensor in a memory; and
wherein the control unit is further programmed to receive RFID tag data from the second RFID reader regarding an item located in a non-temperature controlled second drawer, determine from the received RFID tag data whether an item residing in the second drawer requires a particular temperature, and if the control unit determines that an item residing in the second drawer does require a particular temperature, then provide an alert that a temperature-controlled item has been placed in the second drawer.

18. The cabinet for storing medical items of claim 17 wherein the control unit is further programmed to receive RFID tag data that comprises an identification of the tag and access a data base that correlates RFID tag identification data to a particular item and from a data base, determine whether the identified item has a temperature requirement and if so, control the TEC device in accordance therewith.

19. A method of storing medical items, comprising:
storing medical items in a plurality of drawers in a medical cabinet, each of which is configured to move into and out of a respective cavity to a closed position within the cavity and to an open position in which the drawer is at least partially outside of the cavity;
mounting a thermo-electric cooling ("TEC") device to provide cooling only to a first drawer located in a first cavity;
insulating the first cavity from a second cavity located adjacent the first cavity to inhibit cooling provided to the first drawer in the first cavity from reaching the second cavity and second drawer and tending to keep the second cavity and drawer at ambient temperature;
sensing temperature in the first drawer and logging temperature readings over time;
reading RFID tag data from an RFID tag disposed on an item located in the first drawer to determine if a temperature requirement exists for the item to which the tag is attached;
if a temperature requirement is determined to exist for the item in the first drawer, controlling the temperature in the first drawer with the TEC device to satisfy the temperature requirement;
reading RFID tag data from an RFID tag disposed on an item located in the second drawer to determine if a temperature requirement exits for the item to which the tag is attached;
if it is determined that the item in the second drawer has a temperature requirement, proofing an alert that a temperature-controlled item has been placed in the second drawer.

20. The method of storing medical items of claim 19 wherein:
- the step of reading RFID tag data from an RFID tag disposed on an item located in the first drawer comprises reading with a first RFID reader; and
- the step of reading RFID tag data from an RFID tag disposed on an item located in the second drawer comprises reading with a second RFID reader that is separate from the first RFID reader.

* * * * *